(12) United States Patent
Rothman et al.

(10) Patent No.: US 6,387,389 B1
(45) Date of Patent: May 14, 2002

(54) SUSTAINED-RELEASE DERIVATIVES OF HYDROXYLATED ANALOGS OF SUBSTITUTED 1-[2[BIS(ARYL)METHOXY]ETHYL]-PIPERAZINES AND -HOMOPIPERAZINES AND THEIR USE

(75) Inventors: Richard B. Rothman; Kenner C. Rice, both of Bethesda; David Lewis, Rockville, all of MD (US); Dorota Matecka, Washington, DC (US); John R. Glowa, Shreveport, LA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/269,926

(22) PCT Filed: Oct. 31, 1997

(86) PCT No.: PCT/US97/19758

§ 371 Date: Jun. 30, 1999

§ 102(e) Date: Jun. 30, 1999

(87) PCT Pub. No.: WO98/18769

PCT Pub. Date: May 7, 1998

Related U.S. Application Data

(60) Provisional application No. 60/030,248, filed on Oct. 31, 1996.

(51) Int. Cl.$^7$ ................. A61F 13/00; C07D 241/00; C07D 401/00; A61K 31/495; A61P 25/30

(52) U.S. Cl. ............. 424/422; 424/465; 514/252.11; 514/252.13; 514/253.05; 514/253.06; 514/253.12; 514/254.02; 514/254.05; 514/254.09; 514/254.1; 514/254.11; 514/255.04; 544/357; 544/360; 544/363; 544/366; 544/368; 544/370; 544/373; 544/376; 544/379; 544/380; 544/384; 544/385; 544/397

(58) Field of Search ................. 544/357, 360, 544/363, 366, 368, 370, 373, 376, 379, 380, 384, 385, 397; 514/252.11, 252.13, 253.05, 253.06, 253.12, 254.02, 254.05, 254.09, 254.1, 254.11, 255.04; 424/422, 465

(56) References Cited

U.S. PATENT DOCUMENTS

| | | | |
|---|---|---|---|
| 3,408,356 A | 10/1968 | Horovitz | 260/294.3 |
| 4,476,129 A | 10/1984 | Gootjes et al. | 424/250 |
| 5,177,077 A | 1/1993 | Hohlweg et al. | 514/252 |

FOREIGN PATENT DOCUMENTS

| | | |
|---|---|---|
| DE | 2719246 | 11/1977 |
| DE | 3024305 | 1/1981 |
| EP | 0099148 | 2/1988 |
| WO | WO 91/01732 | 2/1991 |

OTHER PUBLICATIONS

Pettersson, Studies of Four Novel Diphenylbutylpiperazinepyridyl Derivatives on Release and Inhibition of Reuptake of Dopamine, Serotonin and Noradrenaline by Rat Brain in vitro, European Journal of Pharmacology, vol. 282, No. 1–3, pp. 131–135, Aug. 1995.*
Baumann et al., *The Journal of Pharmacology and Experimental Therapeutics*, 271 (3), 1216–1222 (1994).
Glowa et al., *Chemical Abstracts*, 123: 246561g, 86 (1995).
Glowa et al., *Chemical Abstracts*, 123: 246562h, 86 (1995).
Glowa et al., *Experimental and Clinical Psychopharmacology*, 3 (3), 219–231 (1995).
Glowa et al., *Experimental and Clinical Psychopharmacology*, 3 (3), 232–239 (1995).
Glowa et al., *Journal of Medicinal Chemistry*, 39 (24), 4689–4691 (1996).
Matecka et al., *Medicinal Chemistry Research*, 5, 43–53 (1994).
Rothman et al., *Pharmacology Biochemistry and Behavior*, 40, 387–397 (1991).
Rothman et al., *Pharmacology Biochemistry and Behavior*, 43, 1135–1142 (1992).
Rothman et al., *Synapse*, 14, 34–39 (1993).
Rothman, *Life Sciences*, 46, PL–17–PL–21 (1990).
Van Der Zee et al., *Eur. J. Med. Chem.*, 15 (4), 363–370 (1980).
Van Der Zee et al., *Neuropharmacology*, 24 (12), 1171–1174 (1985).

* cited by examiner

*Primary Examiner*—Brenda Coleman
(74) *Attorney, Agent, or Firm*—Leydig, Voit & Mayer, Ltd.

(57) ABSTRACT

The present invention provides sustained-release derivatives of hydroxylated analogs of substituted 1-[2[bis(aryl)methoxy]ethyl]-piperazines and -homopiperazines, pharmaceutical compositions comprising the same, and a method of using such sustained-release derivatives to bind the dopamine transporter to achieve a desired effect, such as antagonism of dopamine reuptake inhibitors, such as cocaine, or dopamine releasers or norepinephrine and/or serotonin reuptake inhibitors, such as methamphetamine.

34 Claims, 4 Drawing Sheets

SUSTAINED-RELEASE DERIVATIVES OF HYDROXYLATED ANALOGS OF SUBSTITUTED 1-[2[BIS(ARYL)METHOXY]ETHYL]-PIPERAZINES AND -HOMOPIPERAZINES AND THEIR USE

CROSS-REFERENCE TO RELATED PATENT APPLICATIONS

This application is a national stage entry under 35 U.S.C. § 371 of PCT/US97/19758, filed Oct. 31, 1997, which claims the benefit of U.S. Provisional Application No. 60/030,248 filed Oct. 31, 1996.

TECHNICAL FIELD OF THE INVENTION

The present invention is directed to sustained-release derivatives of hydroxylated analogs of substituted 1-[2[bis(aryl)methoxy]ethyl]-piperazines and -homopiperazines and their use.

BACKGROUND OF THE INVENTION

Drug abuse is a major public health problem. One of the major drugs of abuse in the U.S. is cocaine. Cocaine is a locomotor stimulant, which acts as a local anesthetic and which inhibits the reuptake of norepinephrine, dopamine and serotonin, presumably by binding to a component of the macromolecular transporter complex that translocates biogenic amines from the synaptic space into the cytosol of the nerve terminus (Galloway, Trends Pharmacol. Sci. 8: 451–454 (1988)). The inhibition of norepinephrine reuptake results in sympathomimetic effects. The euphoric and addictive effects of cocaine, however, appear to result primarily from inhibition of mesolimbic dopamine reuptake (Ritz et al., Science 237: 1219–1223 (1987); Baumann et al., J. Pharmacol. Exper. Ther. 271(3): 1216–1222 (1994)).

Other evidence indicates that mesolimbic dopamine is a crucial neurochemical mediator of rewarding behaviors, e.g., eating and sex (Wise, "Brain dopamine and reward," In Theory in Psychopharmacology, pp. 103–122, Cooper, ed., Academic Press (1981)). In vivo microdialysis studies have demonstrated that the level of extracellular dopamine increases in the nucleus accumbens of animals engaged in rewarding behavior, such as eating (Hernandez et al., Life Sci. 42: 1705–1712 (1988)) or cocaine self-administration (Hurd et al., Neurosci. Lett. 109: 227–233 (1990)). It is believed that the ability of a drug to elevate the level of mesolimbic extracellular dopamine is critical to its abuse (Di Chiara et al., PNAS USA 85: 5274–5278 (1988)) and those drugs that inhibit dopamine reuptake, thereby resulting in addictive and euphorogenic effects, are classified as "type 1 blockers" (Rothman, Life Sci. 46: PL-17–PL-21 (1990)).

Increased use of cocaine in the 1980's (Adams et al., "Cocaine: A growing public health problem" In Cocaine: Pharmacology, Effects and Treatment of Abuse, NIDA Research Monograph 50, Grabowski, ed., U.S. Gov't Printing Office, Washington, D.C. (1984); and Kozel et al., Science 34: 970–974 (1986)) resulted in a parallel increase in cocaine use by opioid-dependent and methadone-maintained patients (Kosten et al., Am. J. Drug Alcohol Abuse 12: 1–16(1986); J. Clin. Psychiatry 48-442–444 (1987); Cushman, Hosp. Community Psychiatry 39: 1205–1207 (1988); and Condelli et al., J. Subst. Abuse Treat. 8: 203–212 (1991)). The increase in use of cocaine has been further compounded by the link between intravenous drug abuse and the spread of HIV. Consequently, public awareness of drug abuse has increased, leading to drug abuse treatment becoming a national priority in the U.S. Accordingly, there is a constant and ever growing need for pharmacotherapies, which enable the treatment of larger numbers of drug abusers than would otherwise be possible with nonpharmacological treatment modalities and which can be coupled with more traditional treatment approaches, such as counseling and rehabilitation.

One pharmacotherapeutic approach is to develop a competitive cocaine antagonist, i.e., a drug that will bind to the dopamine transporter but will not inhibit dopamine reuptake (Rothman et al., Pharma. Biochem. & Behav. 40: 387–397 (1991)). Such a cocaine antagonist would be expected to block cocaine from increasing the level of extracellular dopamine. However, a patient could overcome the inhibitory effect of a competitive cocaine antagonist by self-administering more cocaine.

Another pharmacotherapeutic approach is to develop a noncompetitive cocaine antagonist. The noncompetitive cocaine antagonist would be one that binds to the dopamine transporter with high affinity and dissociates slowly. The noncompetitive cocaine antagonist would then provide a sustained increase in the level of extracellular dopamine, thereby providing the drug abuser with some relief from cocaine-craving due to dopamine deficiency, yet inhibiting cocaine from further elevating the level of extracellular dopamine and increasing the probability of increased toxic side effects.

One such noncompetitive cocaine antagonist is the compound 1-[2-[bis(4-fluorophenyl)methoxy]ethyl]-4-[3-phenylpropyl]piperazine, otherwise known as vanoxerine or GBR 12909 (Rothman et al. (1991), supra; and Rothman et al., WO 91/01732). Vanoxerine is a selective inhibitor of dopamine reuptake and is about 700-fold more potent than cocaine in inhibiting dopamine reuptake in vitro (Andersen, Eur. J. Pharmacol. 166: 493–504 (1989)). Unlike cocaine, however, vanoxerine-inhibited dopamine reuptake does not result in addictive and euphorogenic effects and, thus, vanoxerine is considered to be a "type-II blocker" (Rothman (1990), supra). In addition, although cocaine and vanoxerine produce equivalent motor-stimulating effects, vanoxerine must occupy the dopamine transporter to a greater extent than cocaine in order to produce equivalent behavioral effects (Rothman et al., Pharmacol. Biochem. & Behav. 43: 1135–1142 (1992)). Similarly, although cocaine and vanoxerine cause dose-related elevations in extracellular dopamine when given alone, cocaine causes a rapid and short-lived increase in dopamine, whereas vanoxerine causes a low and sustained elevation of dopamine (Baumann et al. (1994), supra).

Recently, the ability of vanoxerine to inhibit "cocaine-maintained responding" without inhibiting "food-maintained responding" was demonstrated in rhesus monkeys (Macaca mulatta) (Glowa et al., Exper. & Clin. Psychopharmacology 3(3): 219–231 (1995a)). Subsequent studies showed that repeated treatments of rhesus monkeys with lower doses of vanoxerine could sustain these behaviorally-selective effects (Glowa et al., Exper. & Clin. Psychopharmacology 3(3): 232–239 (1995b)).

Another cocaine antagonist is 1-[2-(diphenyl-methoxy)-ethyl]-4-(3-phenylpropyl)homopiperazine, otherwise known as LR1111, which is a homolog of 1-[2-diphenyl-methoxy-ethyl]-4-(3-phenylpropyl)piperazine, otherwise known as GBR12935 (Rothman et al., Synapse 14: 34–39 (1993)). LR1111, which differs from GBR12935 by the addition of a methylene group to the piperazine ring, has affinity for the dopamine transporter similar to that of GBR12935 but with significantly higher selectivity (Rothman et al. (1993), supra). In addition, LR1111 is over 4,000-fold more selective for the dopamine transporter than the serotonin and norepinephrine transporters (Rothman et al. (1993), supra).

Other structurally related dopamine reuptake inhibitors are also known. See, for example, van der Zee et al., *Eur. J. Med. Chem.—Chimica Therapeutica* 15(4): 363–370 (1980); van der Zee et al., *Neuropharmacology* 24(12): 1171–1174 (1985); Gootjes et al., EP 0 099 148 (published Jan. 25, 1984); Gootjes et al., U.S. Pat. No. 4,476,129 (issued Oct. 9, 1984); and Matecka et al., *Med. Chem. Res.* 5: 43–53 (1994).

Unfortunately, some of the above compounds are not suitable for use as pharmacotherapeutic agents because they are not limited in their effect. For example, some of the above compounds have been shown to inhibit both "cocaine-maintained responding" and "food-maintained responding" in monkeys (Glowa et al. (1995b), supra).

Other of the above compounds, although they are limited in effect, are not long-lasting in effect. In other words, use of such compounds requires frequent and regular dosing. Such a characteristic is undesirable for a pharmacotherapeutic agent to be used in the treatment of drug abuse, such as, for example, cocaine abuse, where patient noncompliance is a major issue affecting success of treatment.

In view of the above, there remains a need for a dopamine reuptake inhibitor that binds the dopamine transporter with high affinity, selectivity and specificity and that is long-lasting in effect, such that dosing frequency can be reduced, thereby reducing the potential impact of patient noncompliance on success of treatment. It is an object of the present invention to provide such a compound. In addition, it is an object of the present invention to provide a pharmaceutical composition comprising such a compound. Furthermore, it is an object of the present invention to provide a method of using such a compound to antagonize the effects, e.g., addictive and euphoric effects, of a dopamine reuptake inhibitor, e.g., cocaine, and a norepinephrine and/or serotonin reuptake inhibitor, e.g., methamphetamine. These and other objects and advantages of the present invention will become apparent from the description set forth below.

BRIEF SUMMARY OF THE INVENTION

The present invention provides sustained-release derivatives of hydroxylated analogs of substituted 1-[2[bis(aryl) methoxy]ethyl]-piperazines and -homopiperazines. The hydroxylated analogs of substituted 1-[2-bis(aryl)methoxy] ethyl]-piperazines and -homopiperazines are derivatized for sustained-release by esterification of the hydroxyl group. Preferably, the hydroxyl group is esterified with a medium- to long-chain alkanoic acid. Preferably, the alkanoic acid comprises a $C_{6-20}$ alkyl, $C_{6-20}$ aryl alkyl, or a $C_{6-20}$ cycloalkyl alkyl group. Examples of preferred alkanoic acids include decanoic acid, cyclopentyl propionic acid, phenyl propionic acid, valeric acid, caproic acid, heptanoic acid, and caprylic acid. A preferred substituted piperazine for hydroxylation and subsequent esterification in accordance with the present invention is 1-[2-[bis-(4-fluorophenyl)methoxy]ethyl]-4-[3-phenylpropyl] piperazine. A preferred sustained-release derivative of such a compound is the decanoate ester referred to herein as DBL 583 or, in the alternative, compound 5*, scheme 1, page 53, know as (+/−) 1-[2-[bis-(4-fluoro-phenyl)methoxy]ethyl]-4-[3-phenyl-3-hydroxy-propyl]piperazine. Preferably, the sustained release derivative has a pharmacological half-life of at least about 30 days.

Also provided by the present invention is a pharmaceutical composition comprising such a sustained-release derivative and a pharmaceutically acceptable carrier. Preferably, the pharmaceutical composition is suitable for depot injection into, for example, the buttocks or thigh, such that a continuous release of a small portion of the derivative is continuously released, preferably over at least about 30 days, into the plasma until depleted.

The present invention further provides a method of using such a sustained-release derivative to bind the dopamine transporter as, for example, a noncompetitive antagonist of a dopamine reuptake inhibitor or an antagonist of a dopamine releaser or a norepinephrine and/or serotonin reuptake inhibitor, although the method is useful for other purposes where binding of the dopamine transporter by a present inventive compound has a desired effect. In accordance with the method, the sustained-release derivative is administered to an individual in need of such a compound. The sustained-release derivative is administered in a sufficient amount such that a desired effect is realized. For example, a dopamine reuptake inhibitor or a dopamine releaser or norepinephrine and/or serotonin reuptake inhibitor in the individual is antagonized over a period of time by a sustained release of the derivative during that period of time. Preferably, the compound is administered by depot injection. More preferably, the compound is administered by depot injection into the buttocks or thigh. Preferably, the period of time of antagonism is at least about 30 days. The method is especially useful in the treatment of an individual who abuses cocaine. To the extent that a sustained-release derivative in accordance with the present invention antagonizes a dopamine releaser or an inhibitor of norepinephrine and/or serotonin reuptake, such a derivative, a pharmaceutical composition comprising such a derivative, and a method of administering such a derivative are useful in the treatment of an individual who abuses amphetamines, such as methamphetamine, and phencyclidine.

DETAILED DESCRIPTION OF THE INVENTION

Figure 1:
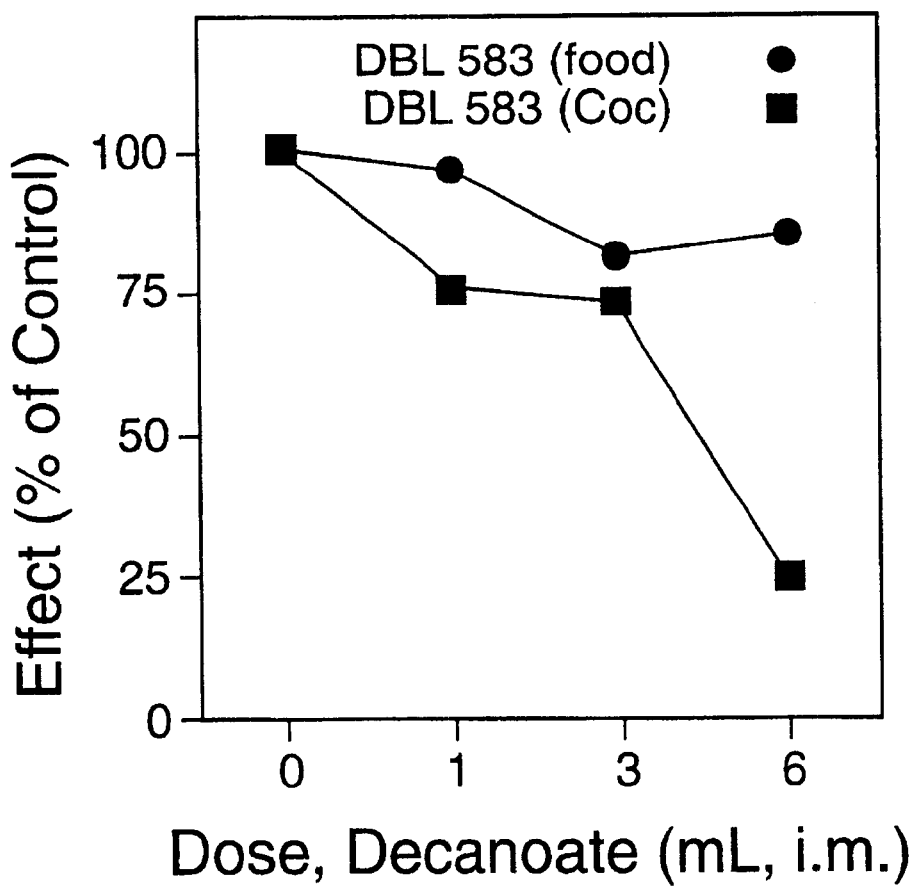
FIG. 1 is a graph of effect (% of control) versus dose of decanoate (compound 5*, i.e., DBL 583, ml intramuscularly), which illustrates the mean effects of a single injection of compound 5* in sesame oil on food-maintained responding and cocaine-maintained responding in rhesus monkeys over 24 days of treatment. The effects are expressed as the mean percent of control rates for food-maintained responding and cocaine-maintained responding, wherein n=2.

The present invention provides compounds and corresponding pharmaceutical compositions useful in the treatment of an individual in need of a compound that binds to the dopamine transporter, wherein such binding has a desired effect, such as antagonism of a dopamine reuptake inhibitor or dopamine releaser or norepinephrine and/or serotonin reuptake inhibitor. Accordingly, the present invention also provides a method of treatment comprising the administration of a compound or a composition to an individual in need thereof. Given that, in one aspect, the present invention addresses the problem of patient noncompliance in the context of drug abuse treatment, in particular cocaine and methamphetamine abuse treatment, the present invention serves to fulfill a long-felt need.

In view of the above, the present invention provides sustained-release derivatives of hydroxylated analogs of substituted 1-[2[bis(aryl)methoxy]ethyl]-piperazines and -homopiperazines. The hydroxylated analogs of substituted 1-[2-bis(aryl)methoxy]ethyl]-piperazines and -homopiperazines are derivatized for sustained-release by esterification of the hydroxyl group.

Esterification of the hydroxyl group is preferably carried out in accordance with the methods set forth herein. Preferably, the hydroxyl group is esterified with a medium- to long-chain alkanoic acid. Preferably, the alkanoic acid comprises a $C_{6-20}$ alkyl, $C_{6-20}$ aryl alkyl, or a $C_{6-20}$ cycloalkyl alkyl group. Examples of preferred alkanoic acids include decanoic acid, cyclopentyl propionic acid, phenyl propionic acid, valeric acid, caproic acid, heptanoic acid, and caprylic acid. The resulting nonpolar, oil-soluble compounds is suitable for depot injection because the high partition coefficient favors the oil phase, resulting in the continuous release of a small proportion of the compound into the plasma, until depleted.

A preferred substituted piperazine for hydroxylation and subsequent esterification in accordance with the present invention is 1-[2-[bis-(4-fluorophenyl)methoxy]ethyl]-4-[3-phenylpropyl]piperazine. A preferred sustained-release derivative of such a compound is the decanoate ester referred to herein as DBL 583 or, in the alternative, compound 5*, scheme 1, page 53, know as (+/−) 1-[2-[bis-(4-fluoro-phenyl)methoxy]ethyl]-4-[3-phenyl-3-hydroxy-propyl]piperazine. Preferably, the sustained release derivative has a pharmacological half-life of at least about 30 days.

Other compounds in accordance with the present invention include those encompassed by the following general structural formulas:

FORMULA 1

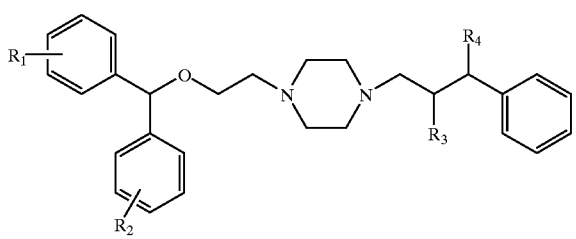

wherein each of $R_1$ and $R_2$ is one or more of the following substituents:

hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; one of $R_3$ and $R_4$ is hydrogen or hydroxyl and the stereochemistry of $R_3$ and $R_4$ is R, S, or RS.

FORMULA 2 wherein each of $R_1$ and $R_2$ is one or more of the following substituents:

hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl and lower alkynyl; one of $R_3$ and $R_4$ is hydrogen or hydroxyl and the stereochemistry of $R_3$ and $R_4$ is R, S or RS.

FORMULA 3 wherein each of $R_1$ and $R_2$ is one or more of the following substituents:

hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; $R_3$ is 2-, 3-, or 4-hydroxyl, and b—c is a single, double (cis or trans) or triple bond.

FORMULA 4 wherein each of $R_1$ and $R_2$ is one or more of the following substituents:

hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; $R_3$ is 2-, 3-, or 4-hydroxyl, and b—c is a single, double. (cis or trans) or triple bond.

FORMULA 5

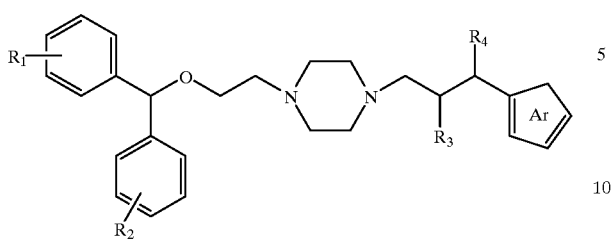

wherein each of $R_1$ and $R_2$ is one or more of the following substituents:
hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; one of $R_3$ and $R_4$ is hydrogen or hydroxyl, the stereochemistry of the hydroxyl is R, S, or RS, and Ar contains 1–4 atoms from the following group: O, N, and S. Examples of Ar include thiophene, furan, imidazole, and tetrazole. Preferably, the sustained-release derivative has a pharmacological half-life of at least about 30 days.

FORMULA 6

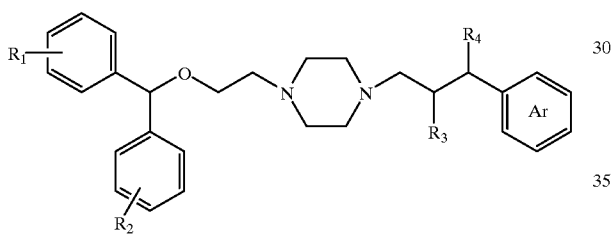

wherein each of $R_1$ and $R_2$ is one or more of the following substituents:
hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; one of $R_3$ and $R_4$ is hydrogen or hydroxyl, the stereochemistry of the hydroxyl is R, S, or RS, and Ar contains 1–4 atoms from the following group: O, N, and S. Examples of Ar include pyridine and pyrazine.

FORMULA 7

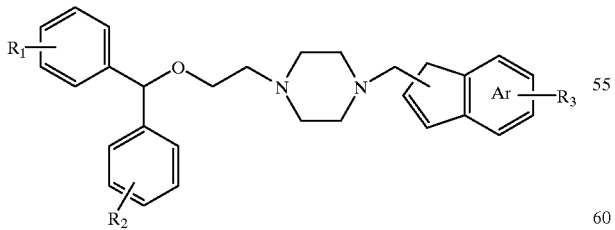

wherein each of $R_1$ and $R_2$ is one or more of the following substituents:
hydrogen, hydroxyl, loweralkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; $R_3$ is hydroxyl at positions 1–7 on Ar; and Ar contains 1–4 atoms from the following group: O, N, and S. Examples of Ar includes indole, benzofuran, and benzoxazole.

FORMULA 8

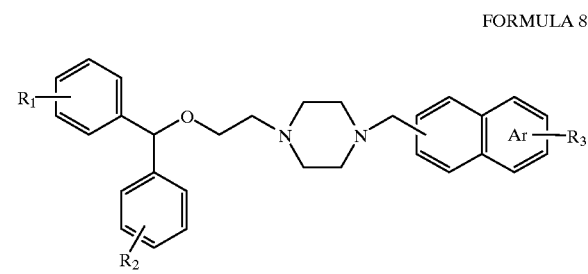

wherein each of $R_1$ and $R_2$ is one or more of the following substituents:
hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; $R_3$ is hydroxyl at positions 1–8 on Ar; and Ar contains 1–4 atoms from the following group: O, N, and S. Examples of Ar includes quinoline and isoquinoline.

FORMULA 9

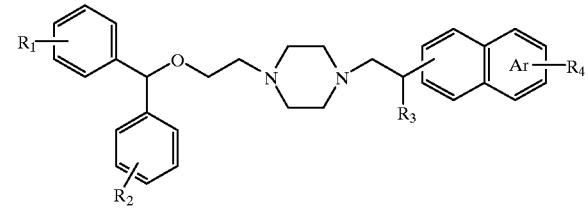

wherein each of $R_1$ and R2 is one or more of the following substituents:
hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; $R_3$ is hydrogen or hydroxyl and the stereochemistry of the hydroxyl is R, S, or RS; and $R_4$ is hydrogen or hydroxyl at positions 1–8 on Ar. Examples of Ar include indole, benzofuran, and benzoxazole.

FORMULA 10

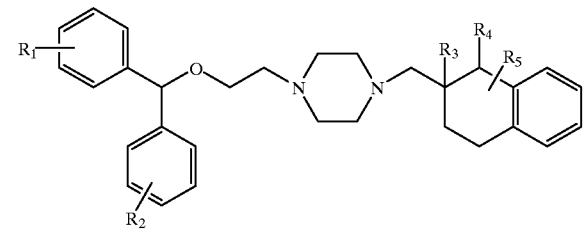

wherein each of $R_1$ and $R_2$=one or more of the following substituents:
hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; $R_3$ is hydrogen or lower alkyl; $R_4$ is hydroxyl; $R_5$ is hydrogen, lower alkyl, aryl, or aryl alkyl; and the stereochemistry of $R_3$, $R_4$ and $R_5$ is R, S, or RS.

FORMULA 11

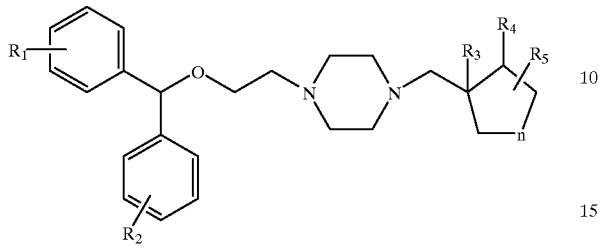

wherein each of $R_1$ and $R_2$ is one or more of the following substituents:

hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl;

$R_3$ is hydrogen; $R_4$ is hydroxyl; $R_5$ is hydrogen, lower alkyl, aryl, or aryl alkyl; the stereochemistry of $R_3$, $R_4$, and $R_5$ is R, S, or RS; and n is $(CH_2)$, $(CH_2)_2$ or $(CH_2)_3$ and can be substituted by $R_5$.

FORMULA 12

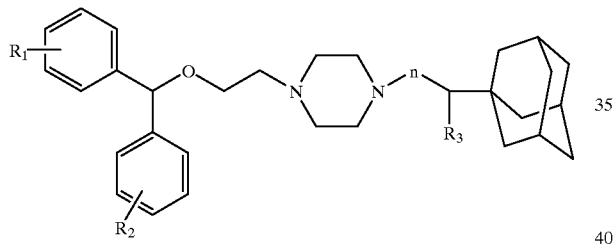

wherein each of $R_1$ and $R_2$ is one or more of the following substituents:

hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl;

$R_3$ is hydroxyl; n=$(CH_2)$, $(CH_2)_2$ or $(CH_2)_3$ and the stereochemistry of $R_3$ is R, S, or RS.

FORMULA 13

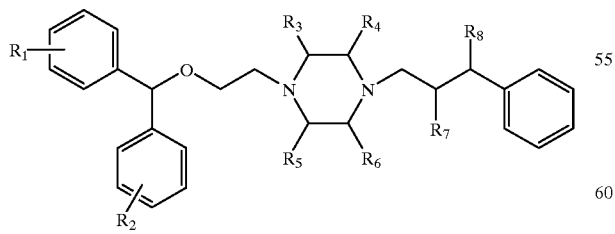

wherein each of $R_1$ and $R_2$ is one or more of the following substituents:

hydrogen, hydroxyl, lower alkyl, cycloalkyl, cycloalkyl alkyl, lower alkoxy halo, halo lower alkyl, hydroxy lower alkyl, amino, lower alkyl mono amino, lower alkyl di amino, lower alkanoyl, lower alkenyl, and lower alkynyl; each of $R_3$-$R_6$ is hydrogen, hydroxyl, lower alkyl, cycloalkyl, cycloalkyl alkyl, halo, halo lower alkyl, lower alkoxy, hydroxy lower alkyl, lower alkenyl, and lower alkynyl; and each of $R_7$ and $R_8$ is hydrogen or hydroxyl. The stereochemistry of $R_3$-$R_8$ is R, S, or RS.

FORMULA 14

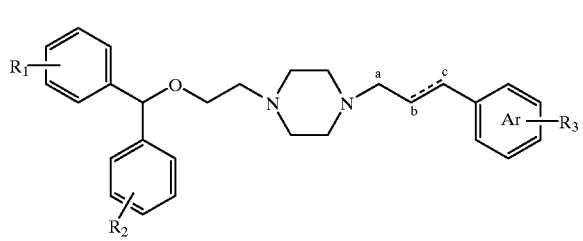

wherein each of $R_1$ and $R_2$ is one or more of the following substituents:

hydrogen, hydroxyl, lower alkyl, cycloalkyl, cycloalkyl alkyl, lower alkoxy halo, halo lower alkyl, hydroxy lower alkyl, amino, lower alkyl mono amino, lower alkyl di amino, lower alkanoyl, lower alkenyl, and lower alkynyl; $R_3$ is hydroxyl at positions 2–6 on Ar; Ar contains 1–4 atoms from the following group: O, N, and S; and b—c is a single, double (cis or trans) or triple bond. Examples of Ar include pyridine and pyrazine.

FORMULA 15

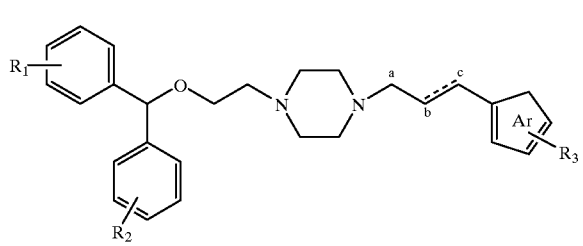

wherein each of $R_1$ and $R_2$ is one or more of the following substituents:

hydrogen, hydroxyl, lower alkyl, cycloalkyl, cycloalkyl alkyl, lower alkoxy, halo, halo lower alkyl, hydroxy lower alkyl, amino, lower alkyl mono amino, lower alkyl di amino, lower alkanoyl, lower alkenyl, and lower alkynyl; $R_3$ is hydroxyl at positions 2–5 on Ar; and Ar contains 1–3 atoms from the following group: O, N, and S; and b—c is a single, double (cis or trans) or triple bond. Examples of Ar include thiophene, furan, and imidazole.

With respect to the above-described general structural formulas, $R_1$ and $R_2$ can be a lower alkyl group, such as a $C_{1-4}$ alkyl, a lower alkoxy group, such as a $C_{1-7}$ alkoxy, a lower alkyl monoamino, such as a $C_{1-7}$ alkyl monoamino, a lower alkyl diamino, such as a $C_{1-7}$ alkyl diamino, a lower alkanoyl, such as a $C_{1-7}$ alkanoyl, an alkenyl, such as a $C_{1-7}$ alkenyl, or an alkynyl, such as a $C_{1-7}$ alkynyl.

Compounds encompassed by the above-described general structural formulas can be synthesized in accordance with the following general structural reaction schemes:

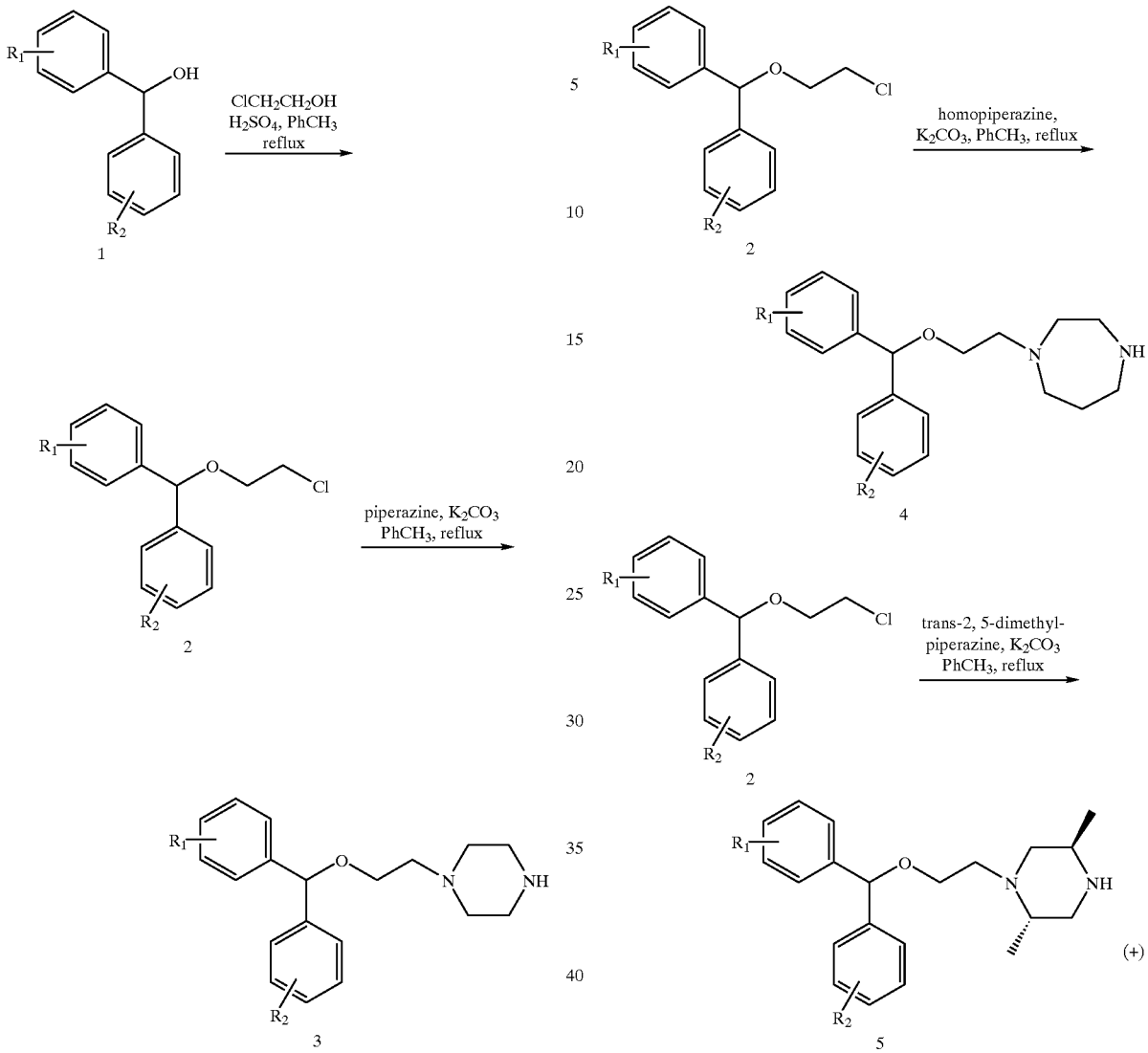

With respect to compound 3, $R_1=R_2=H$; $R_1=R_2=$p-F; $R_1=H$, $R_2=$o-Me; $R_1=H$, $R_2=$o-OMe; $R_1=R_2=$—$CH_2$; or $R_1=R_2=$—$CH_2CH_2$—.

With respect to the above reaction schemes, sometimes it is necessary to use a milder acid, e.g., p-toluene sulfonic acid, in lieu of sulfuric acid in the conversion of compound 1 to compound 2.

General Structural Reaction Schemes For
Compounds Encompassed By Formula 1

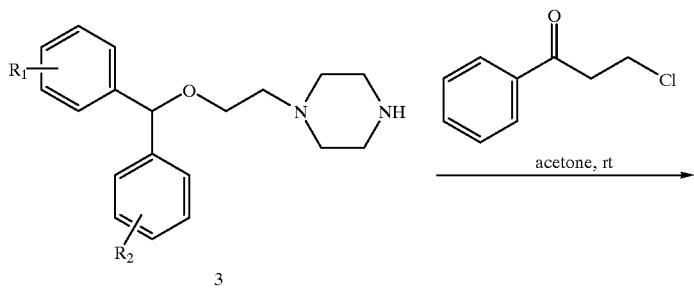

-continued
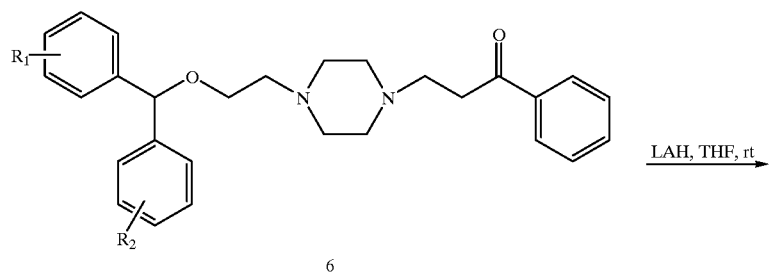
6
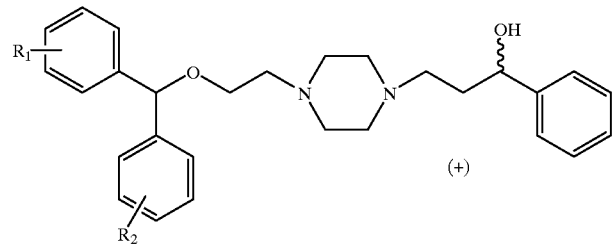
7
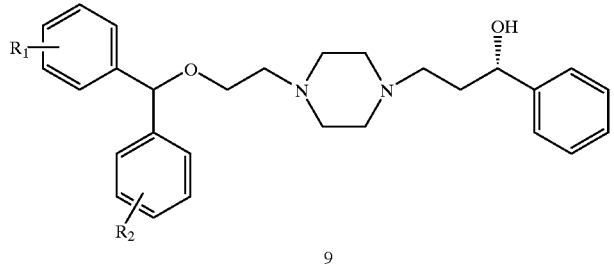
8
or
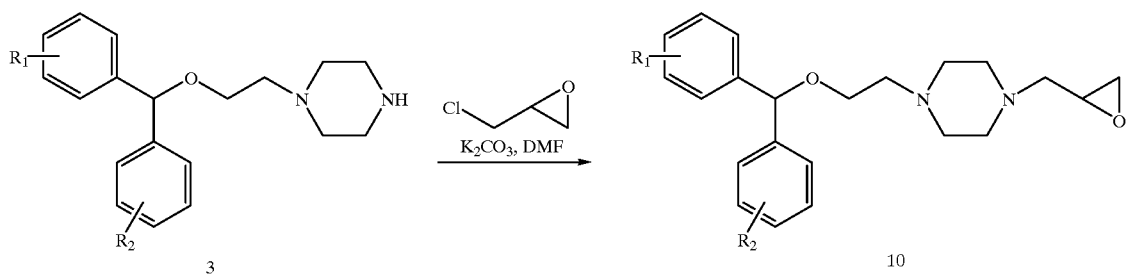
9
R- or S- compound formed depending on which enantiomer of B-chlorodiisopinocampheylborane (DIP-chloride) is used.

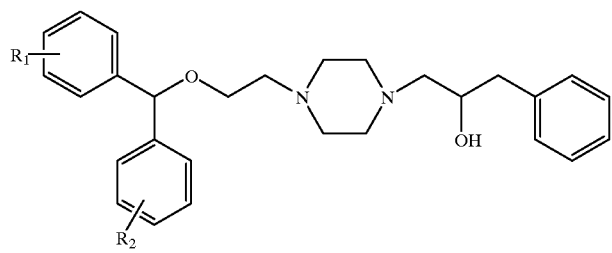
11
Note: 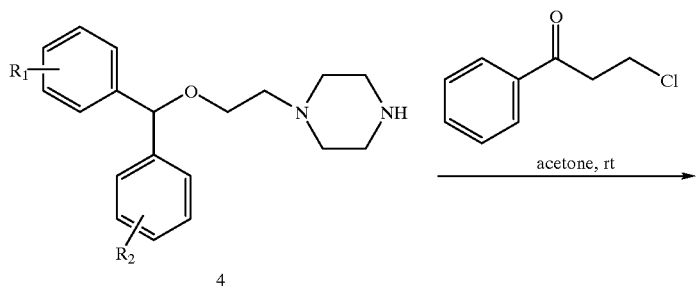 is used to get the enantiomers of 10 and 11. Cl-[epoxide] is used to get racemic 11.
General Structural Reaction Schemes For
Compounds Encompassed By Formula 2
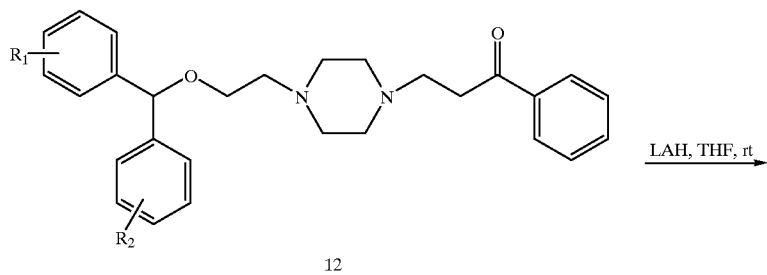
4
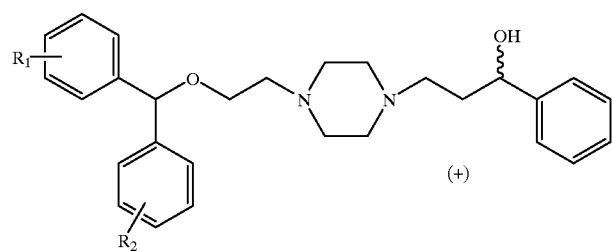
12
[LAH, THF, rt]
13

-continued
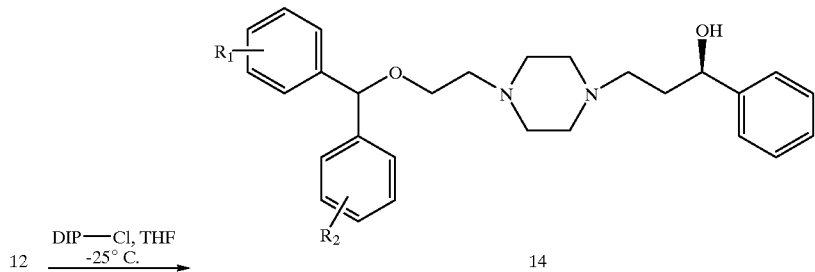
14
or
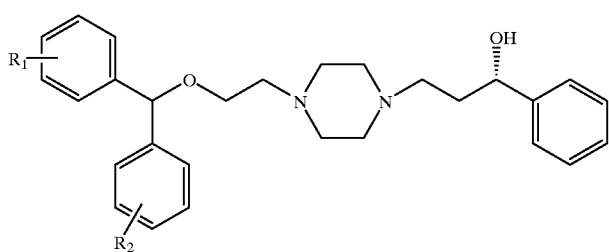
15
R- or S- compound formed depending on which DIP-chloride is used.
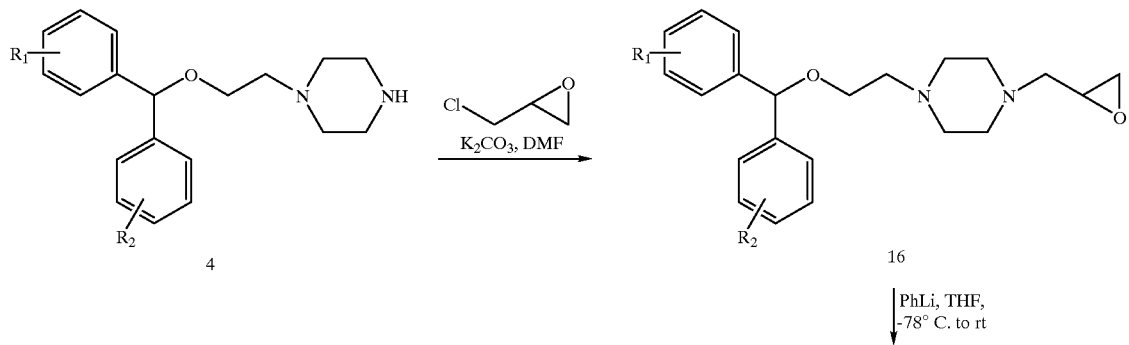
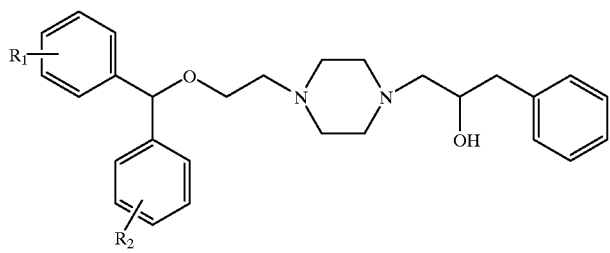
17
Note:  is used to get the enantiomers of 16 and 17. Cl⌒⌒O is used to get racemic 17.

General Structural Reaction Schemes For
Compounds Encompassed By Formula 3
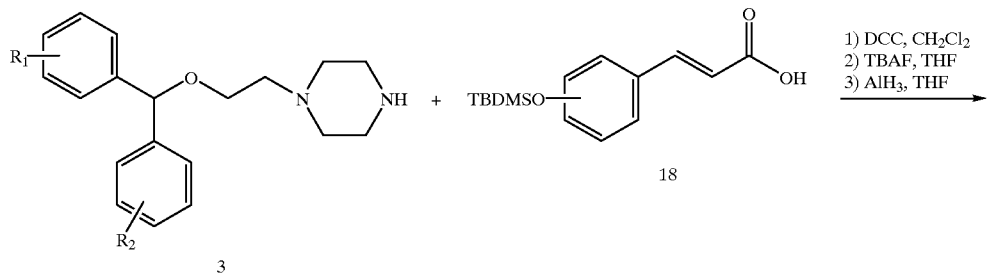
18
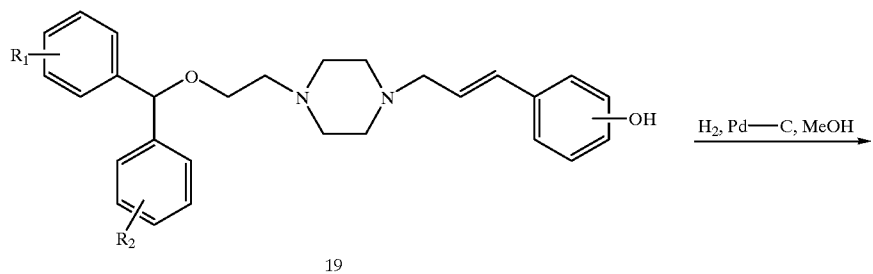
19
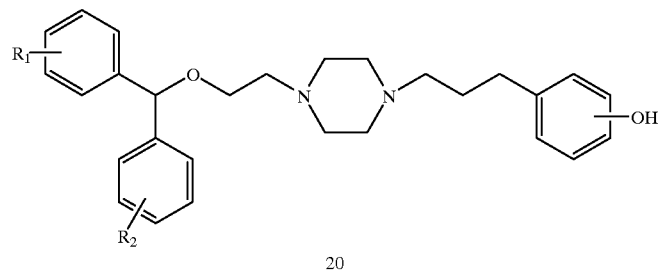
20
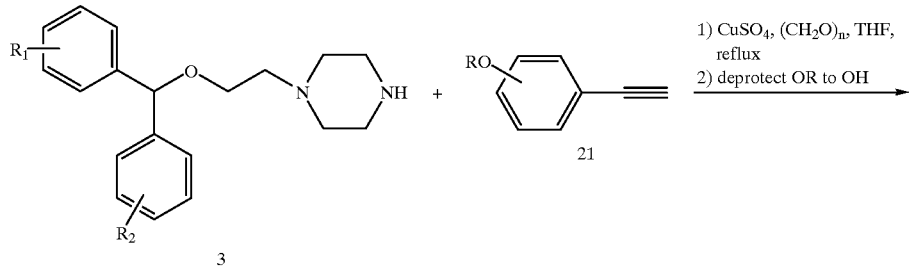
21
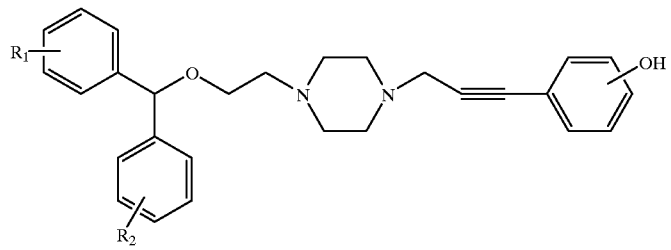
22

General Structural Reaction Schemes For
Compounds Encompassed By Formula 4
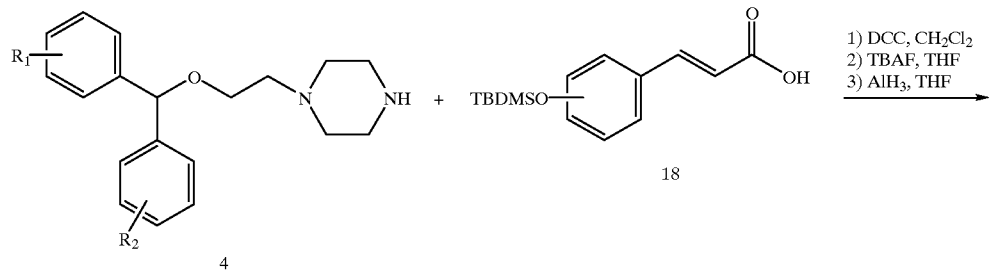
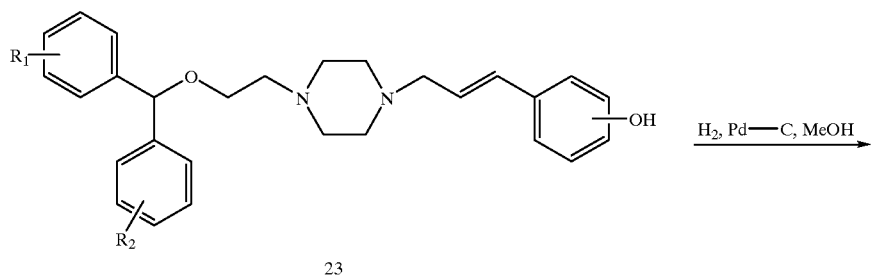
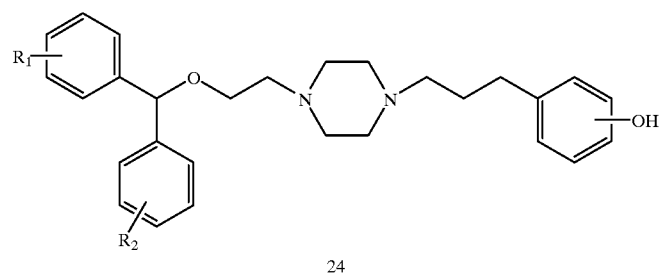
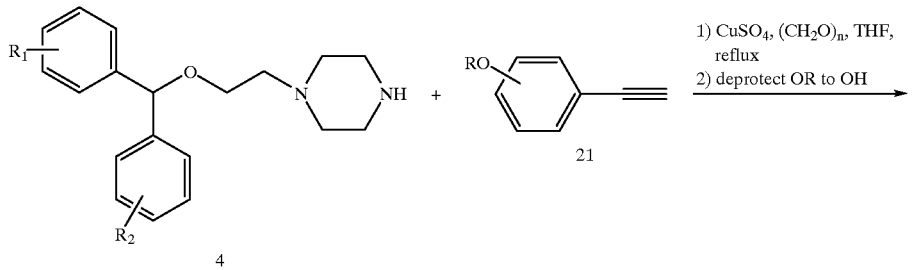
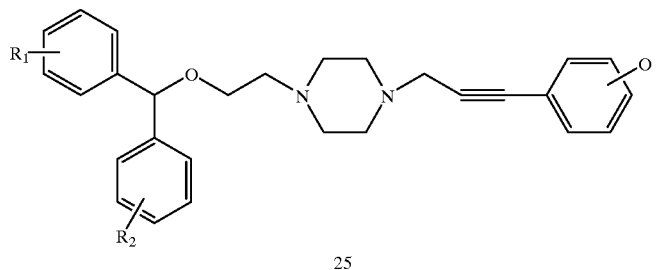

General Structural Reaction Schemes For
Compounds Encompassed By Formula 5
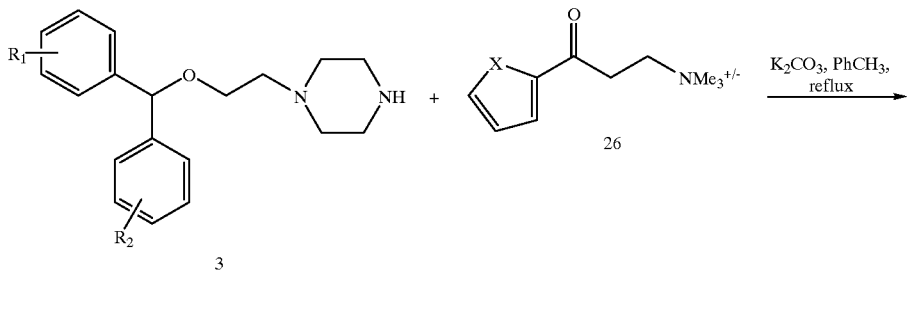
26
3
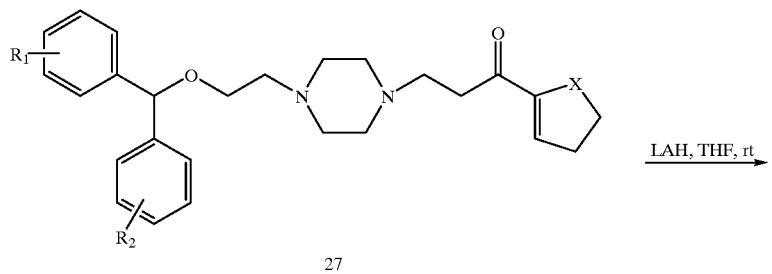
27
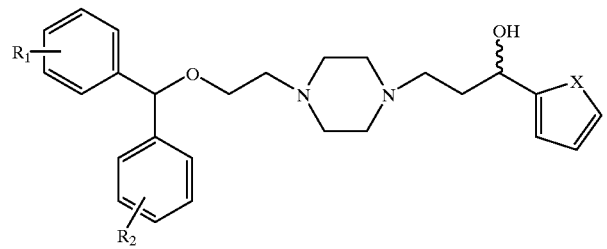
28
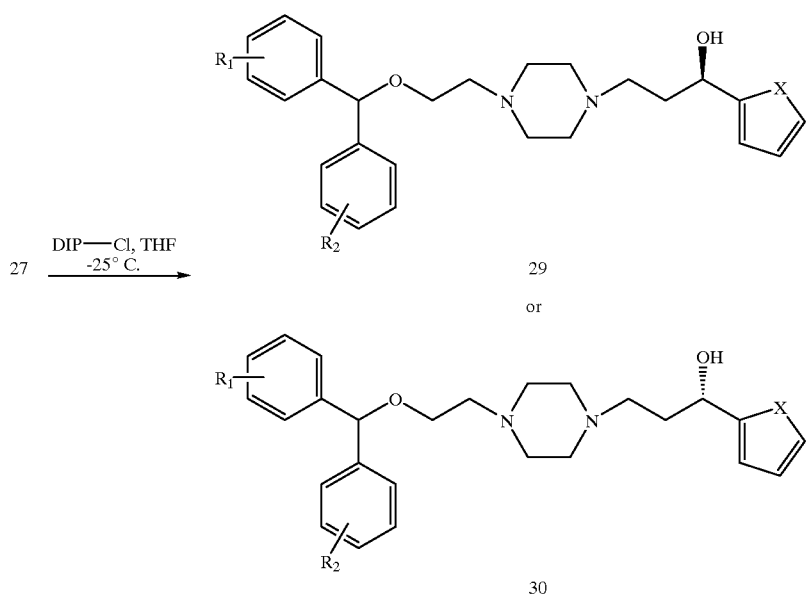
29
or
30
R- or S- compound formed depending on which
enantiomer of DIP-chloride is used.

-continued
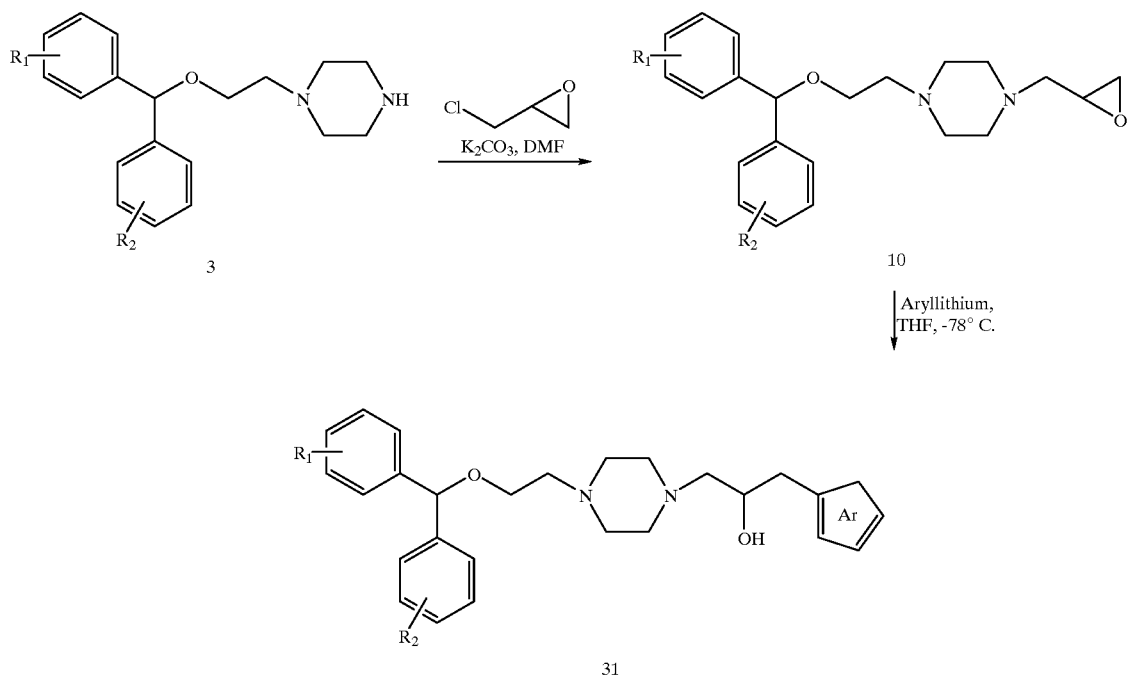
Note: image or image is used to get the enantiomers of 10 and 13. image is used to get racemic 31.
General Structural Reaction Schemes For
Compounds Encompassed By Formula 6
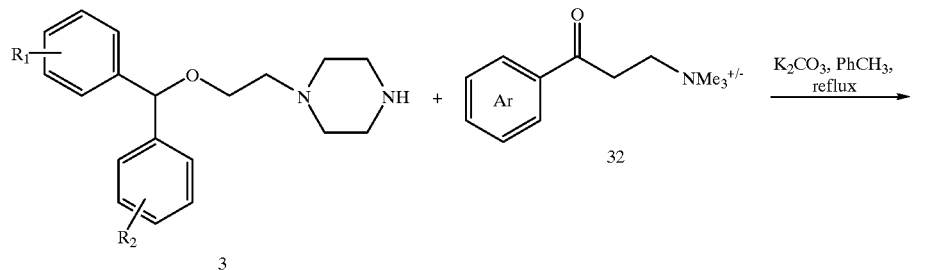
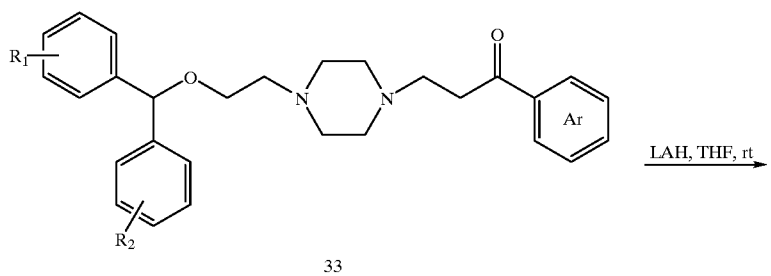

-continued
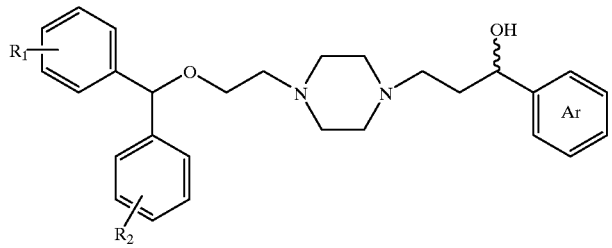
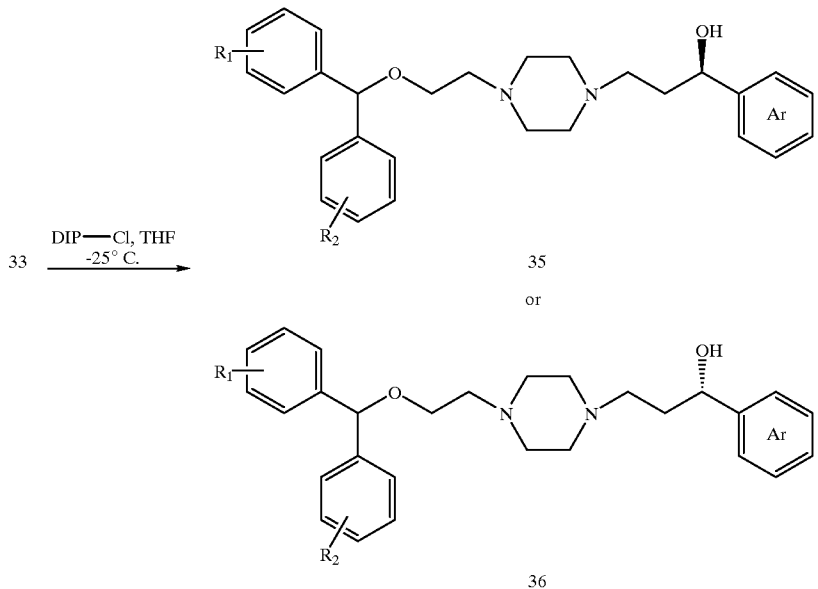
R- or S- compound formed depending on which DIP-chloride is used. Ar is a six-membered hetero-aromatic ring or a substituted phenyl.
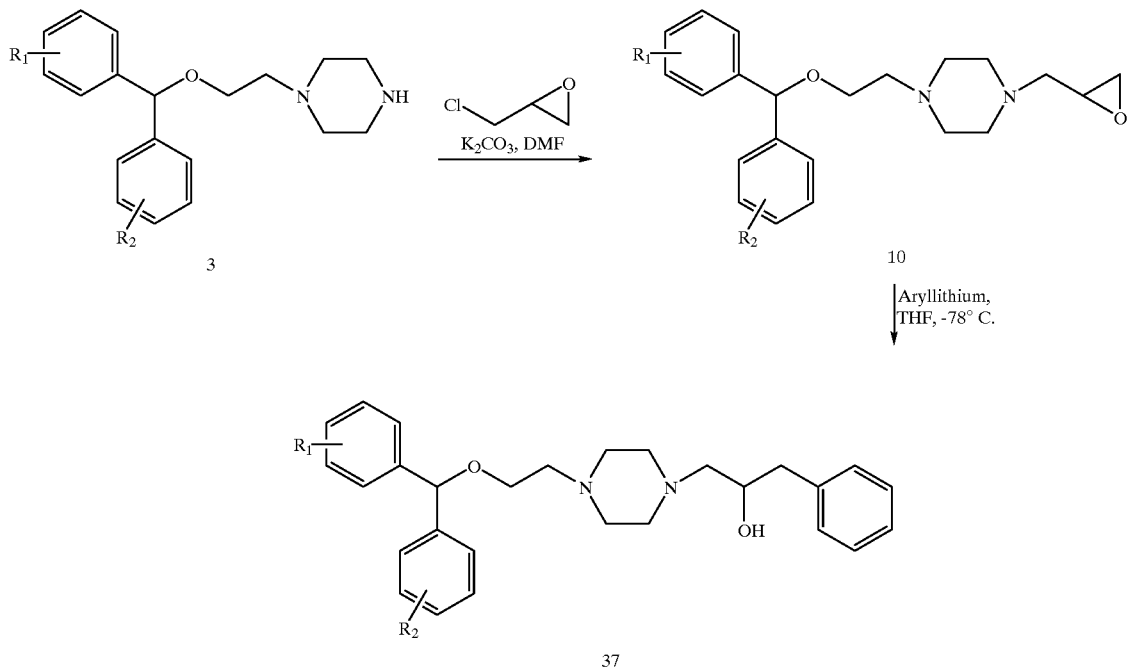

-continued
Note: 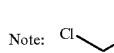 is used to get the enantiomers of 10 and 31.  is used to get racemic 37.
General Structural Reaction Scheme For Compounds Encompassed By Formula 7
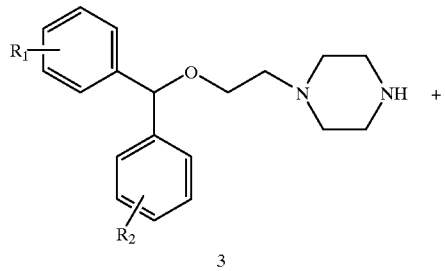
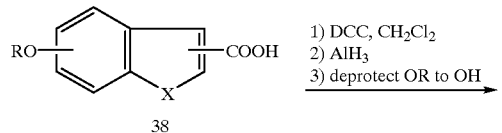
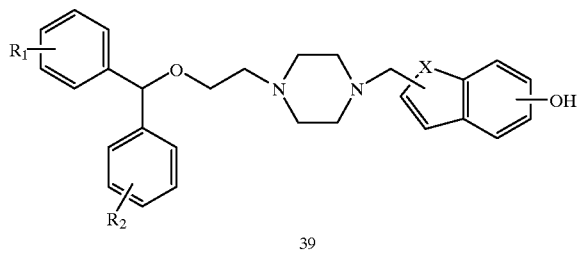
General Structural Reaction Scheme For Compounds Encompassed By Formula 8
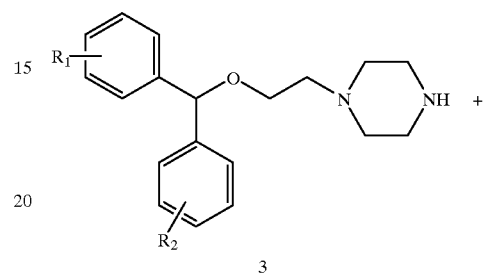
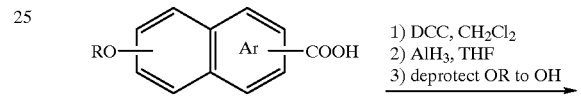
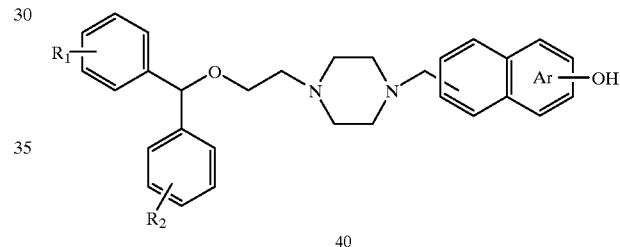
General Structural Reaction Scheme For Compounds Encompassed By Formula 9
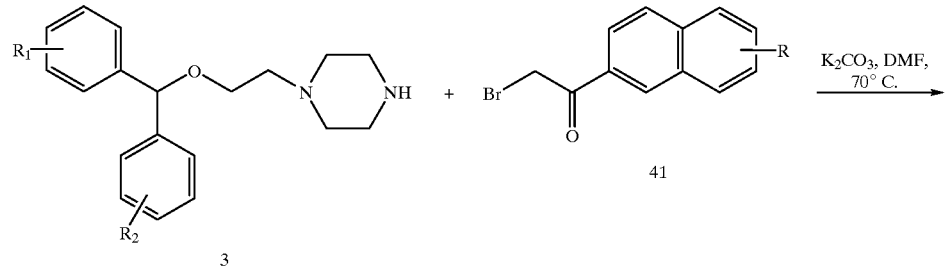
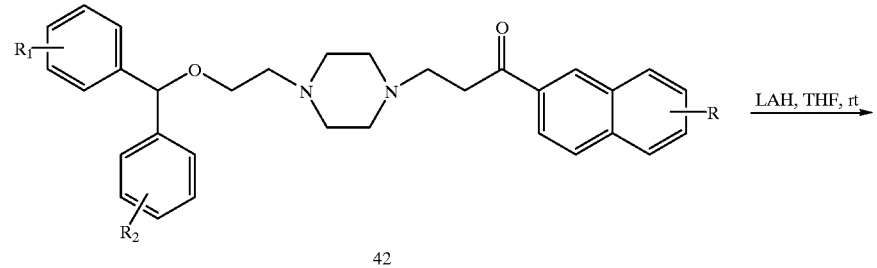

-continued
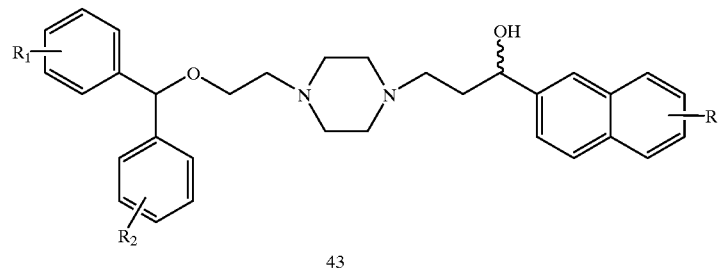
43
With respect to the above reaction schemes, compounds 42 and 43 can be made via the reactions schemes set forth above with respect to general structural formulas 5 and 6.
General Structural Reaction Schemes For
Compounds Encompassed By Formula 10
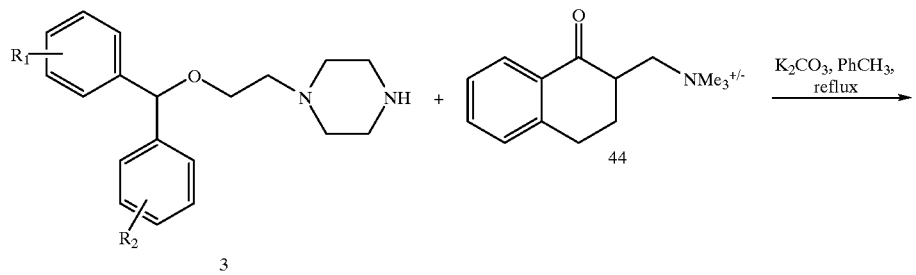
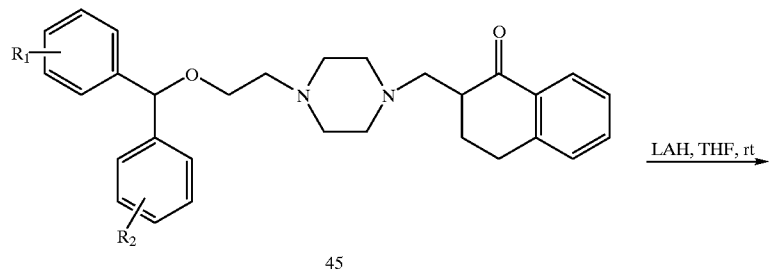
45
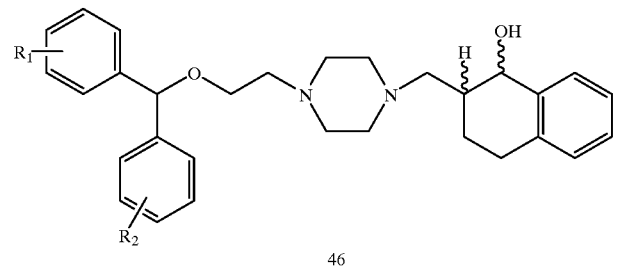
46
cis- and trans-
separable by silica
gel chromatography -continued
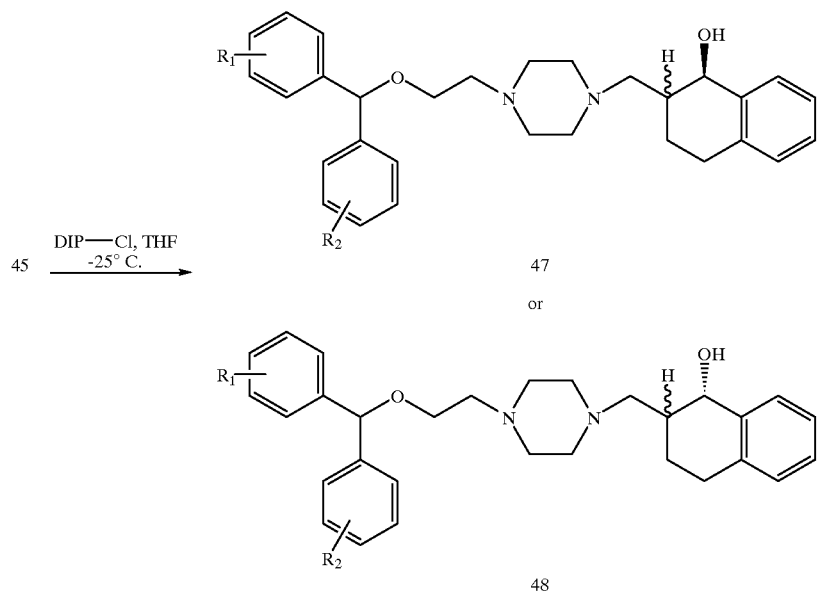
The stereochemistry of the hydroxyl group is R or S depending on which DIP-chloride is used.
General Structural Reaction Scheme For Compounds Encompassed By Formula 11
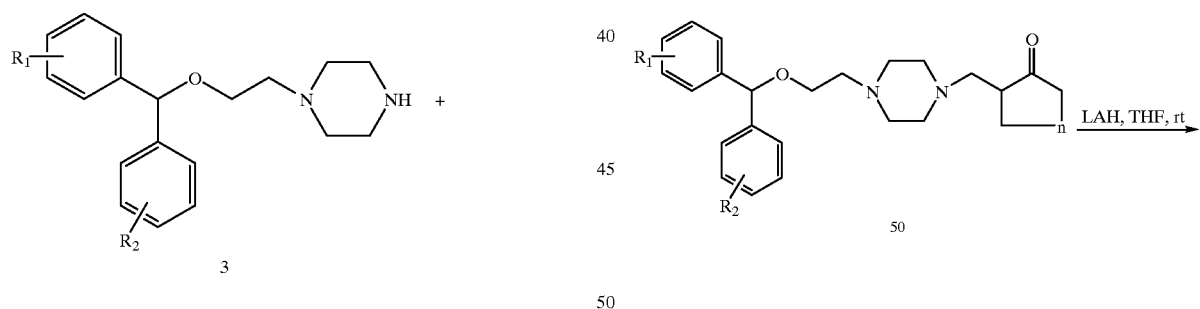
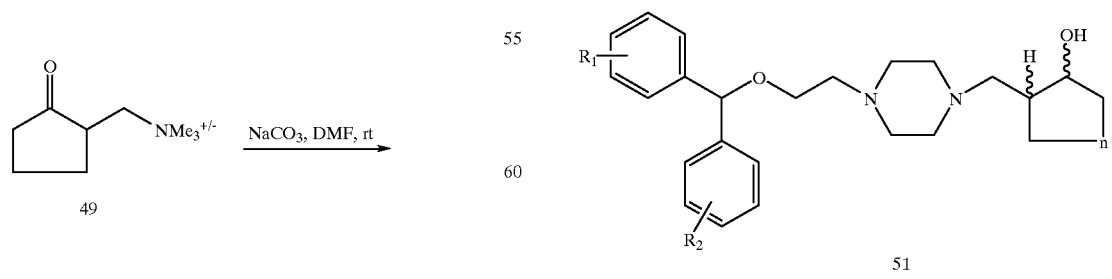

General Structural Reaction Schemes For
Compounds Encompassed By Formula 12
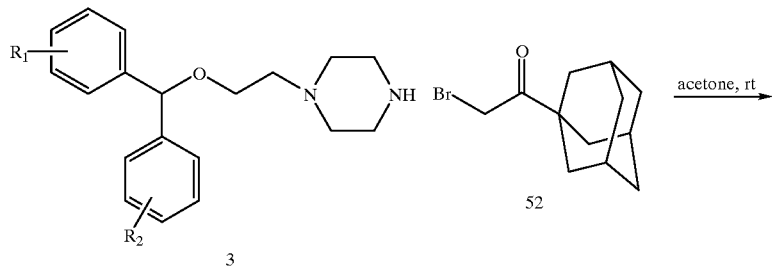
3   52   acetone, rt →
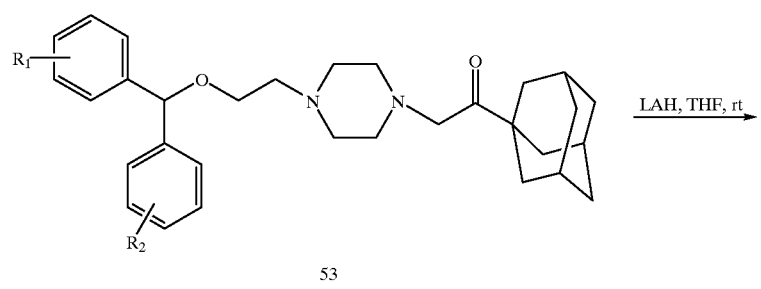
53   LAH, THF, rt →
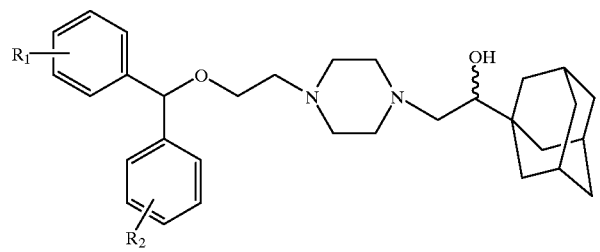
54
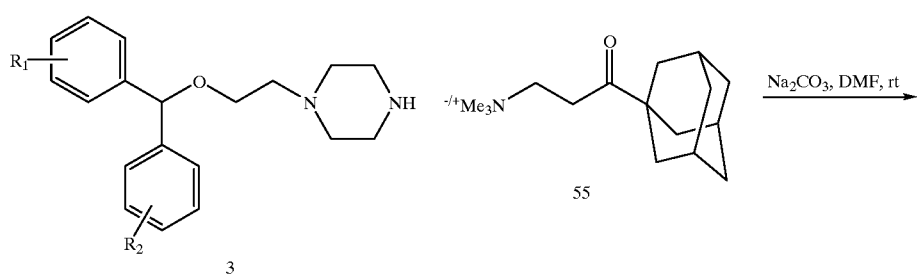
3   55   Na$_2$CO$_3$, DMF, rt →
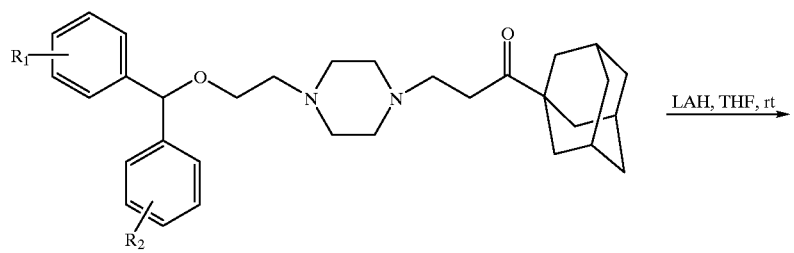
56   LAH, THF, rt →

-continued
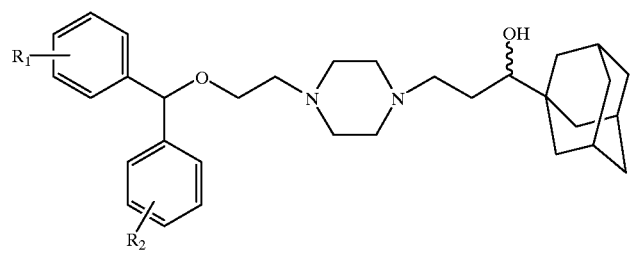
57
General Structural Reaction Schemes For
Compounds Encompassed By Formula 13
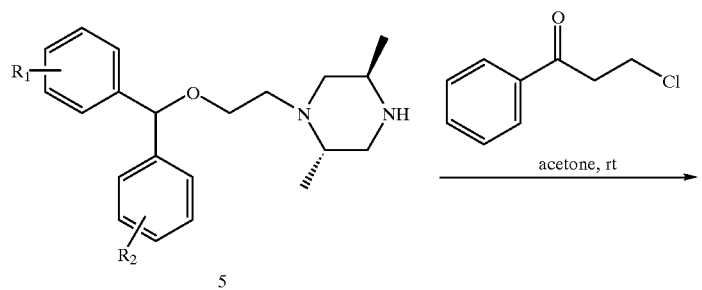
5
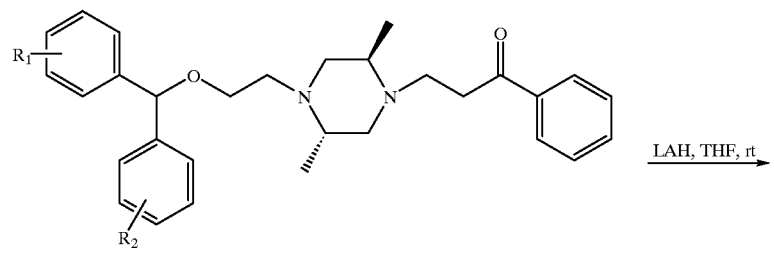
58
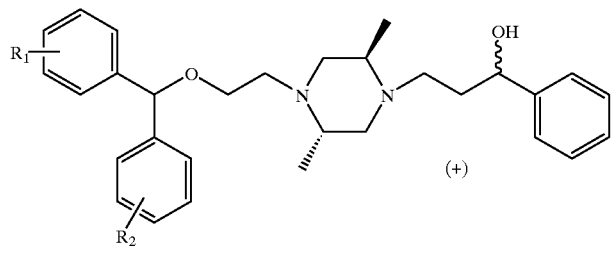
59
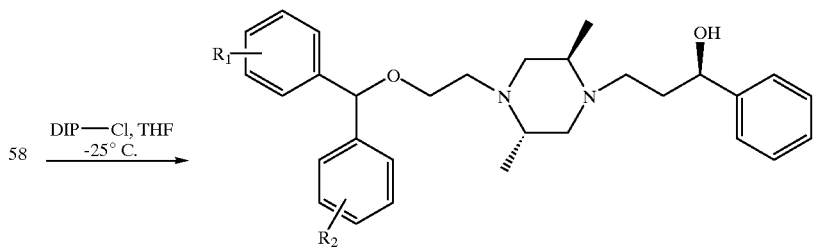
60
or -continued
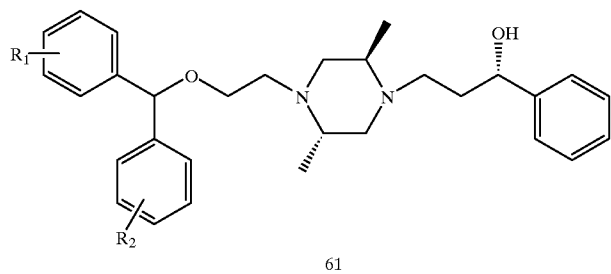
61
The stereochemistry of the hydroxyl group is R or S depending on which DIP-chloride is used.
General Structural Reaction Scheme For
Compounds Encompassed By Formula 14
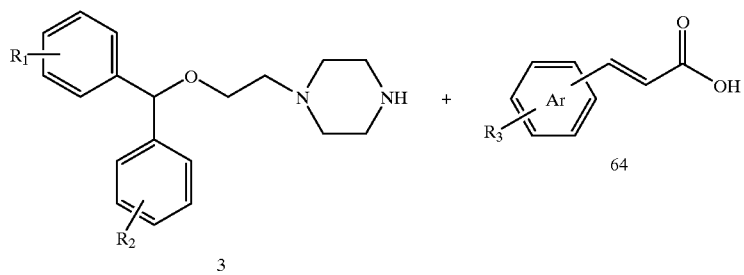
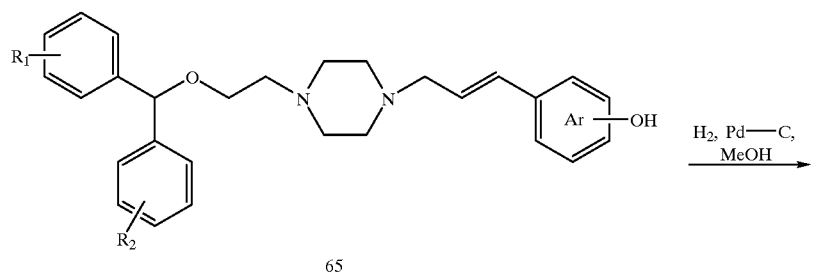
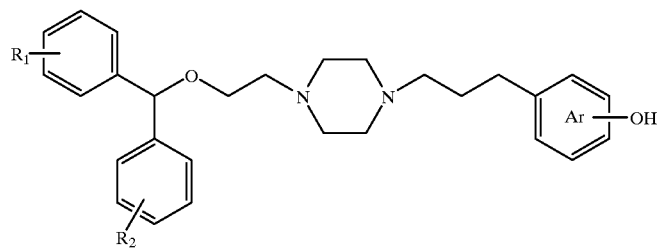
66

General Structural Reaction Scheme For
Compounds Encompassed By Formula 15

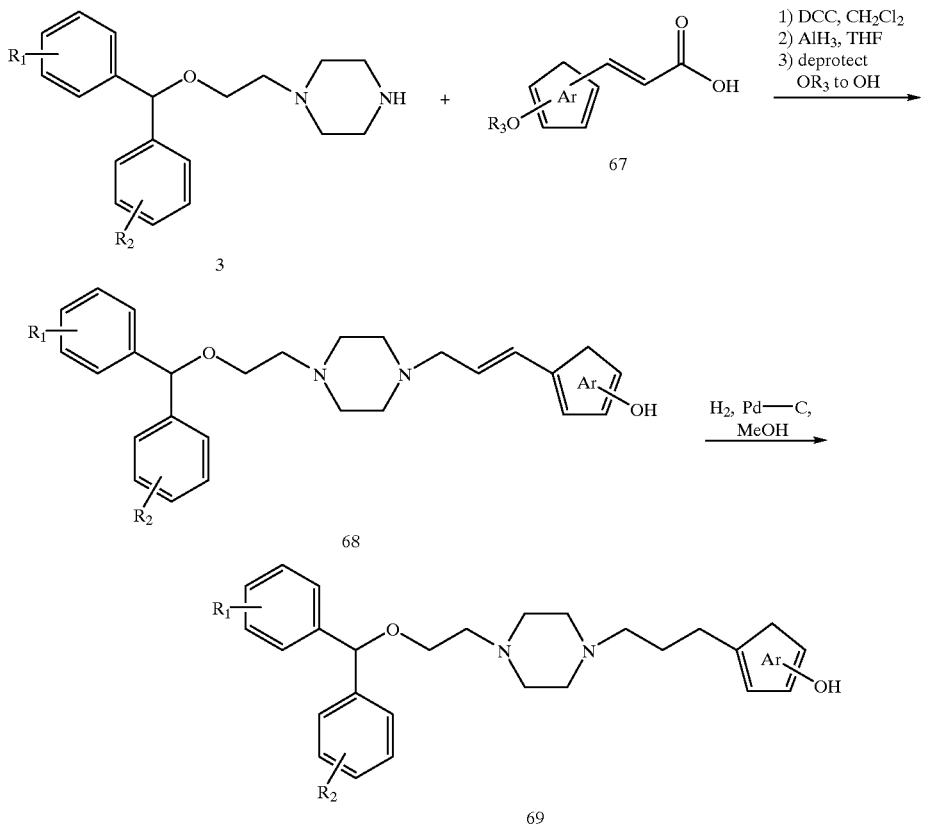

The above-described compounds can be converted to an ester, such as the decanoate derivative, in accordance with the following general structural reaction scheme:

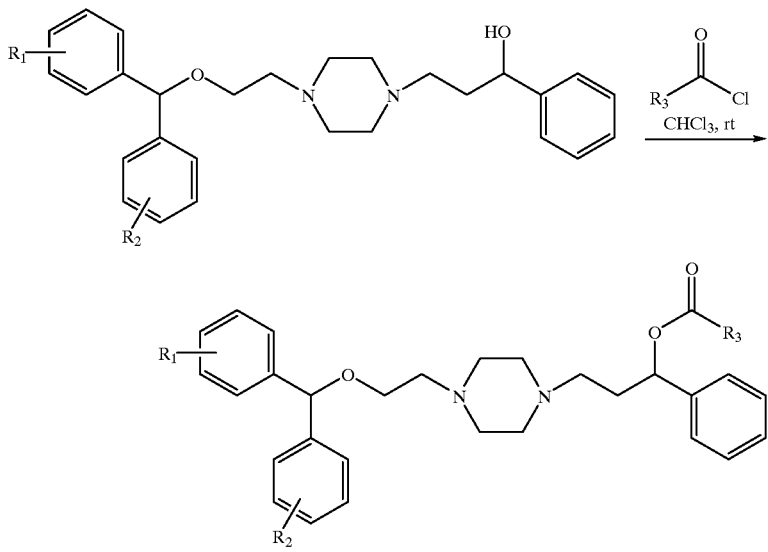

wherein each of $R_1$ and $R_2$ is one or more of the following substituents: hydrogen, hydroxyl, lower alkyl, cycloalkyl, cycloalkyl alkyl, lower alkoxy halo, halo lower alkyl, hydroxy lower alkyl, amino, lower alkyl mono amino, lower alkyl di amino, lower alkanoyl, lower alkenyl, and lower alkynyl; and $R_3$ is lower alkyl, cyclo alkyl, cycloalkyl alkyl, or alkyl.

With respect to the above-described general structural reaction scheme for conversion of an above-described compound to an ester, $R_3$ of the esterifying acid is a $C_{6-20}$ alkyl, $C_6$–$C_{20}$ aryl alkyl, or a $C_{6-20}$ cycloalkyl alkyl.

Specific examples of compounds encompassed by the above-described general structural formulas, which, in turn, can be synthesized in accordance with the above-described general structural reaction schemes, include the following:

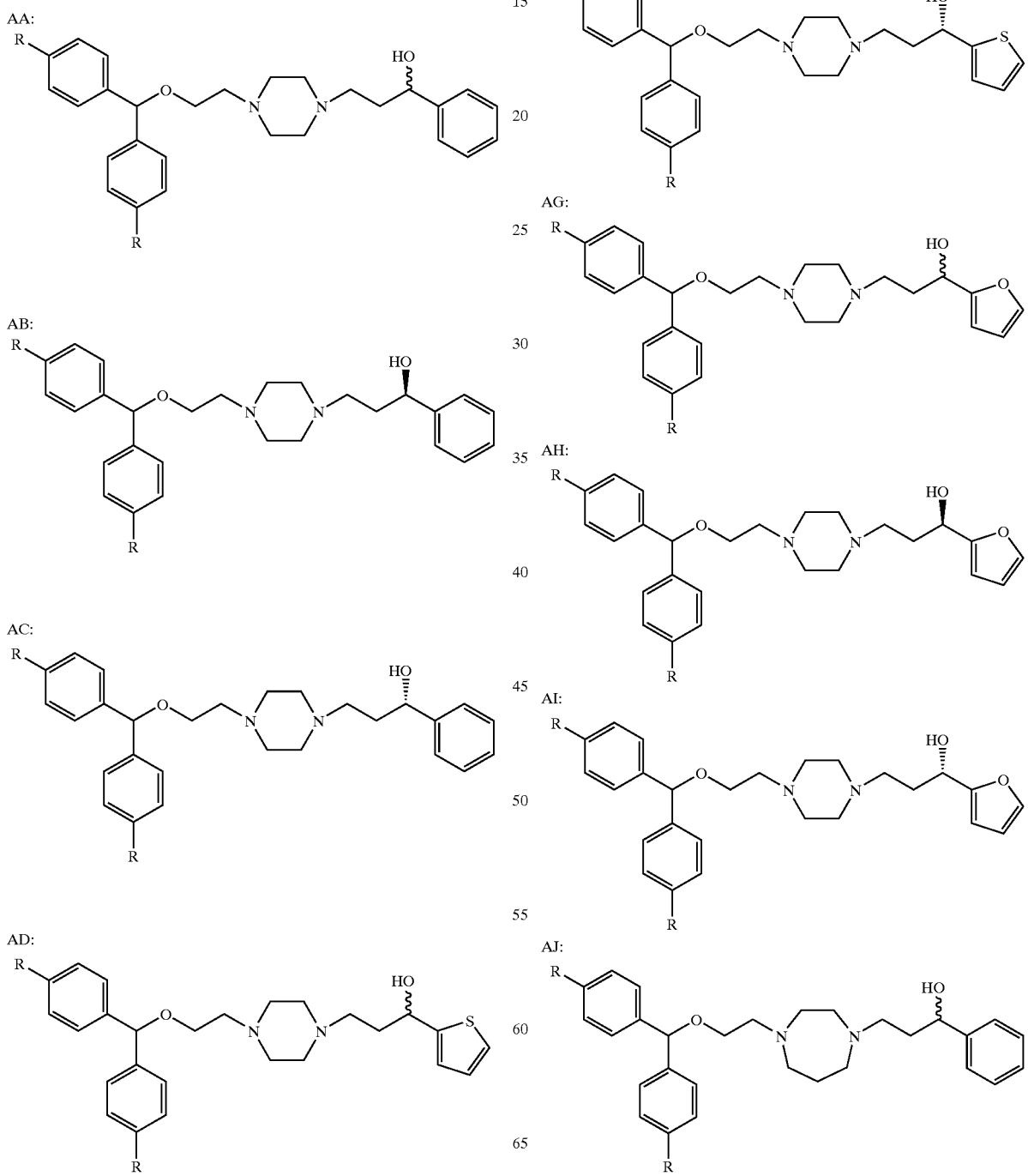

AK:
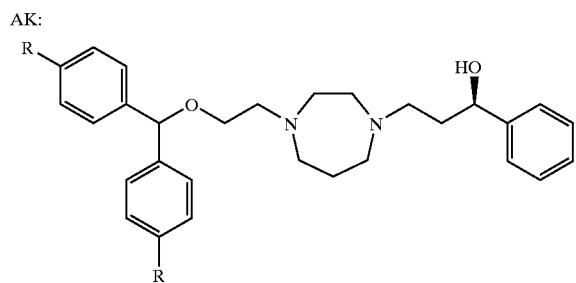
AL:
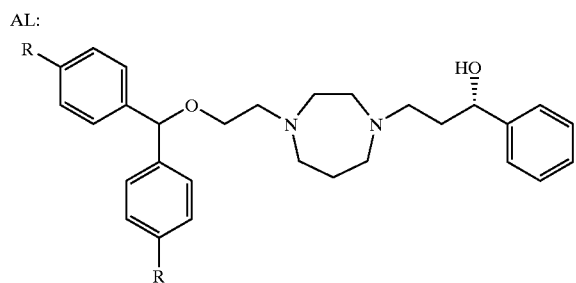
AM:
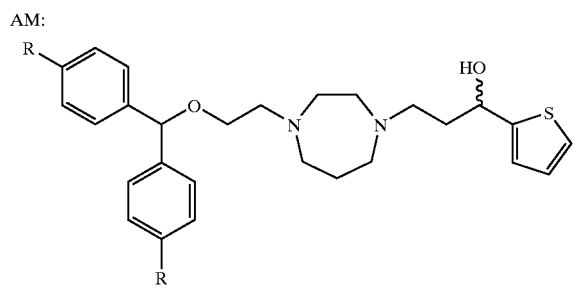
AN:
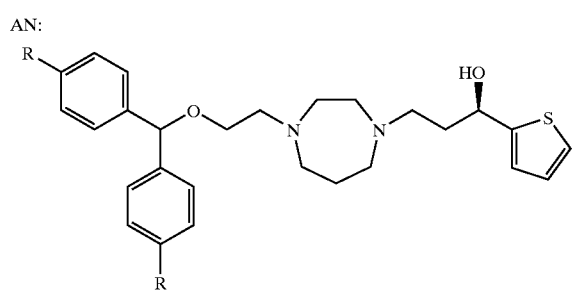
AO:
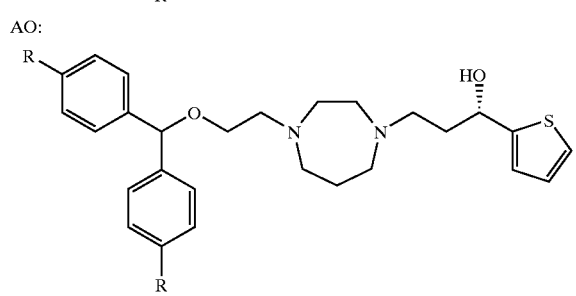
AP:
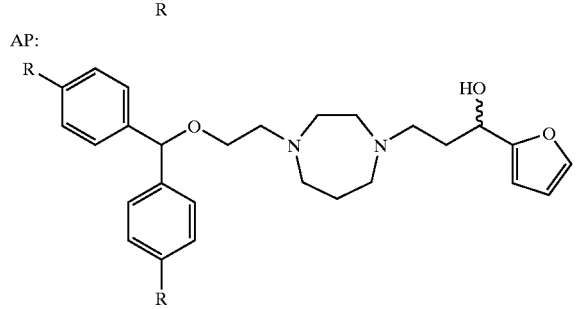
AQ:
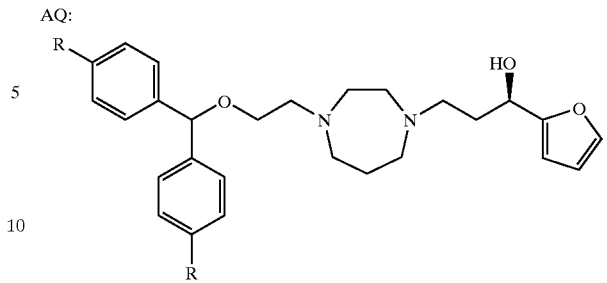
AR:
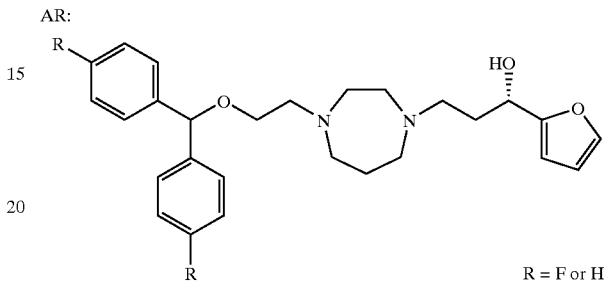
R = F or H
AS:
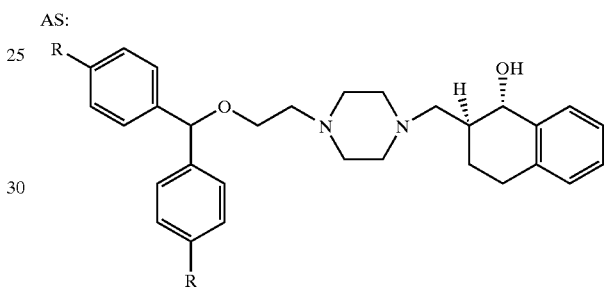
AT:
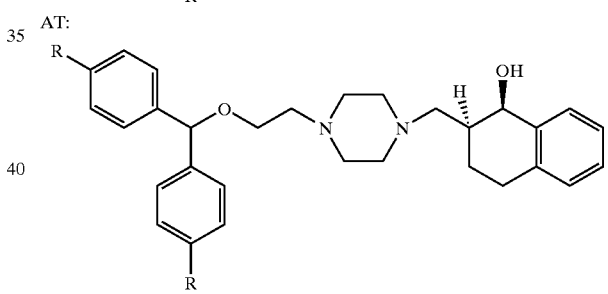
AU:
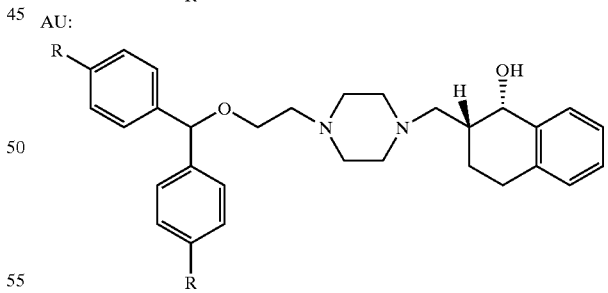
AV:
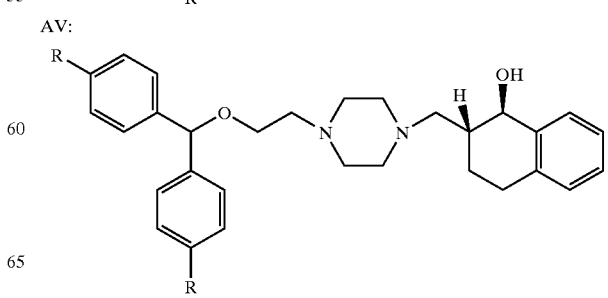

AW:
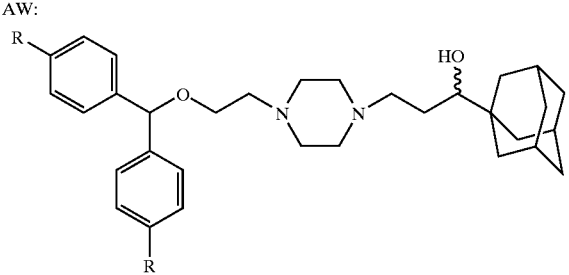
AX:
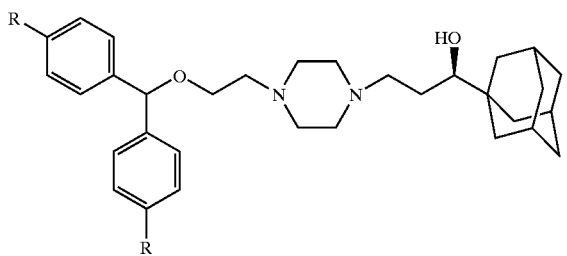
AY:
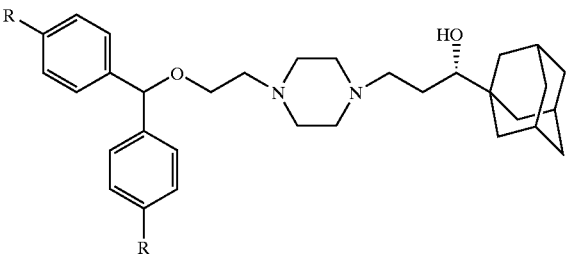
AZ:
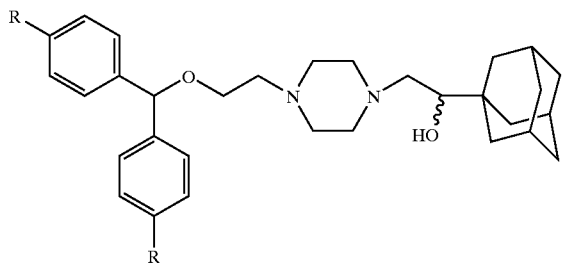
BA:
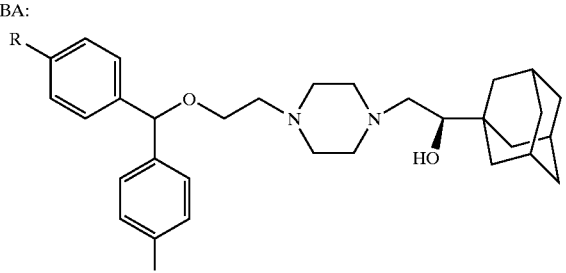
BB:
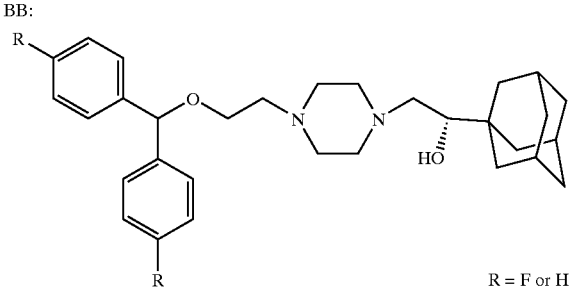
R = F or H
BC:
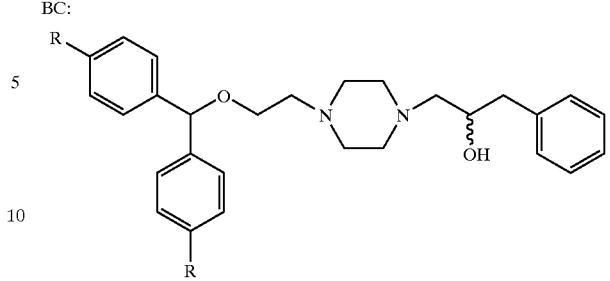
BD:
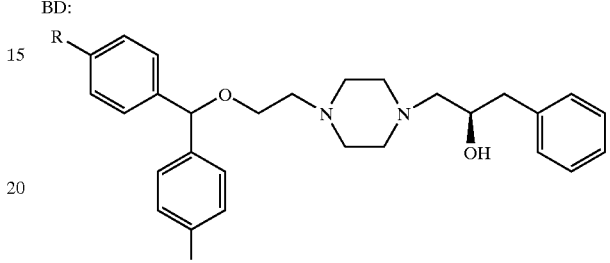
BE:
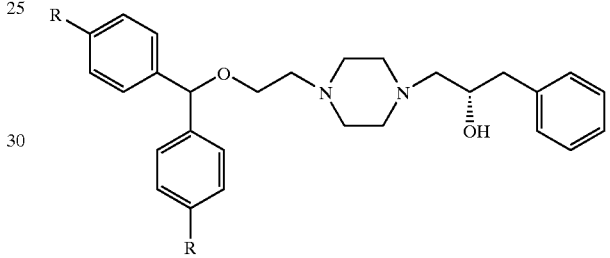
BF:
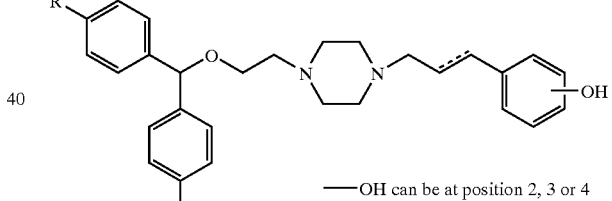
— OH can be at position 2, 3 or 4
===== can be single or double bond
BG:
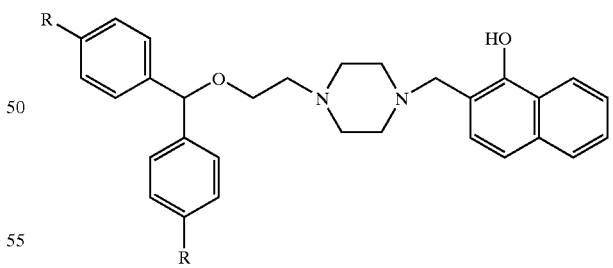
BH:
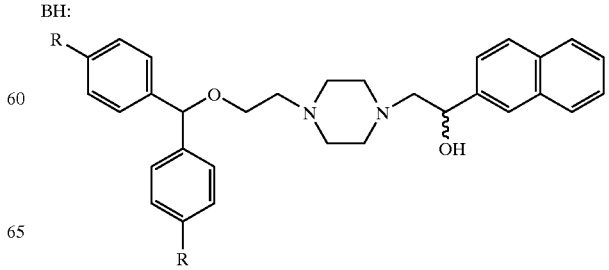

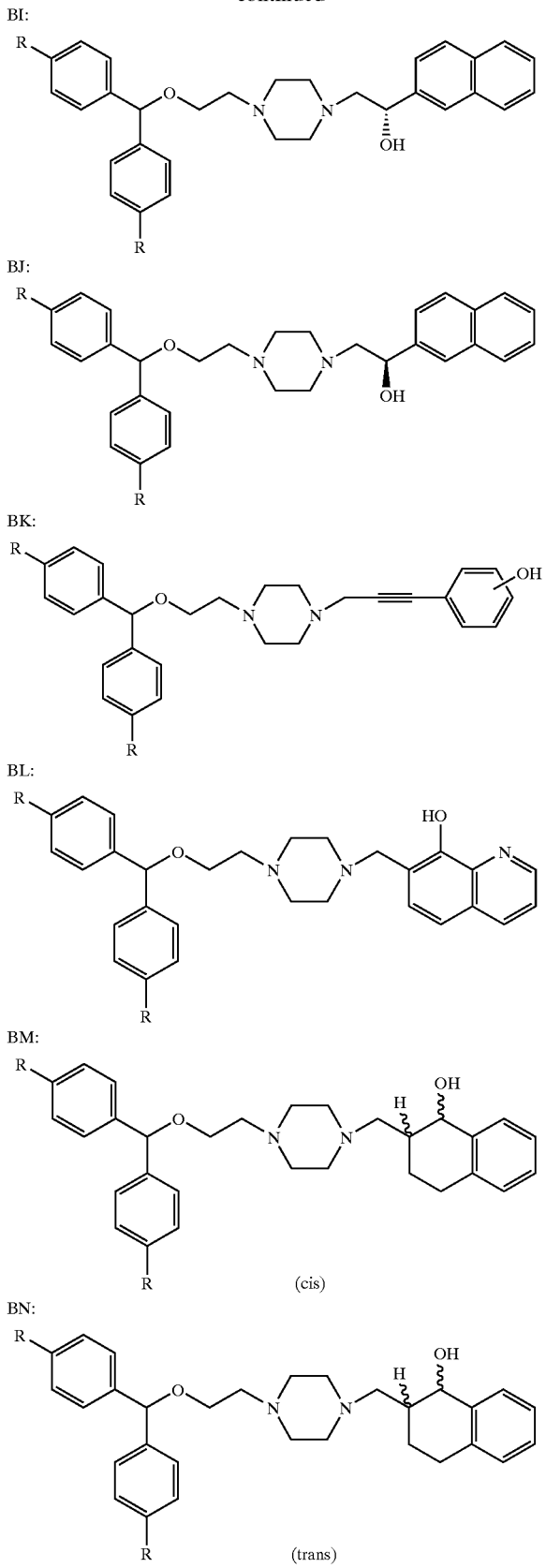

Also provided by the present invention is a pharmaceutical composition comprising such a sustained-release derivative and a pharmaceutically acceptable carrier. Pharmaceutically acceptable carriers for use in such compositions are well-known to those skilled in the art. The choice of carrier will be determined in part by the particular composition, as well as by the particular method, e.g., injection, in particular depot injection, or transdermal patch, used to administer the composition. Accordingly, there is a wide variety of suitable formulations of the pharmaceutical composition of the present invention. Preferably, the pharmaceutical composition is suitable for injection, in particular depot injection, i.e., a large single injection into a site where the composition is sequestered in the body, preferably into the buttocks or the thigh, such that a small portion of the derivative is continuously released, preferably over at least about 30 days, into the plasma until the derivative is depleted. Such methods of injection are known to those skilled in the art. A compound or composition of the present invention also can be combined with other active agents provided the combination retains the desired pharmacotherapeutic effect.

The present invention further provides a method of using such a sustained-release derivative as a noncompetitive antagonist of a dopamine reuptake inhibitor. In accordance with the method, the sustained-release derivative is administered to an individual in need of such a noncompetitive antagonist. The sustained-release derivative is administered in a sufficient amount such that the dopamine reuptake inhibitor in the individual is antagonized over a period of time by a sustained release of the derivative during that period of time. Preferably, the compound is administered by depot injection or transdermal patch. More preferably, the compound is administered by depot injection into the buttocks or thigh. Preferably, the period of time of antagonism is at least about 30 days. The method is especially useful in the treatment of an individual who abuses cocaine and, therefore, the present invention also provides a method of administering to an individual, who abuses cocaine, by depot injection into the buttocks or thigh a pharmaceutical composition, which is suitable for depot injection and which comprises a sufficient amount of a $C_{6-20}$ alkanoate, $C_{6-20}$ aryl alkanoate, or a $C_{6-20}$ cycloalkyl alkanoate ester derivative of a hydroxylated analog of 1-[2-[bis-(4-fluorophenyl)methoxy]ethyl]-4-[3-phenylpropyl]piperazine, preferably the compound referred to herein as DBL 583 or compound 5*, scheme 1, page 53, known as (+/−) 1-[2-[bis-(4-fluorophenyl)methoxy]ethyl]-4-[3-phenyl-3-hydroxy-propyl] piperazine to antagonize the cocaine in the individual over a period of time of at least about 30 days by a sustained release of the compound during that period of time. In this regard, if the volume to be injected is too large for injection at a single site, the dose can be divided for concomitant injection into two or more sites in the body.

The amount of compound sufficient to antagonize a dopamine reuptake inhibitor, such as cocaine, can be determined using noninvasive methods, such as PET and SPECT, to determine the minimum receptor occupancy necessary to decrease the effect of the dopamine reuptake inhibitor, which, in the case of cocaine, for example, is drug-seeking behavior. In this regard, the above compounds can be tested for in vitro and in vivo activity in accordance with the Examples set forth below.

To the extent that a sustained-release derivative in accordance with the present invention antagonizes an inhibitor of norepinephrine reuptake and/or an inhibitor of serotonin reuptake, such a derivative, a pharmaceutical composition comprising such a derivative, and a method of administering such a derivative are useful in the treatment of an individual who abuses amphetamines, such as methamphetamine and phencyclidine.

EXAMPLES

The following examples are intended to illustrate the present invention and are not intended to limit the scope of the present invention. With respect to Example 3, the emerging consensus that more effective pharmacotherapies may reduce drug abuse and AIDS has stimulated interest in the development of preclinical models for the evaluation of medications of potential use in the treatment of drug abuse (Mello et al., *Neuropsychopharmacology* 14(6): 375–424 (1996)). Given that animals will reliably self-administer most drugs that are abused by man and, unlike clinical trials, given that compliance with a given treatment regimen is ensured, the effect of a given medication can be quantitatively evaluated in an animal under controlled experimental conditions with accurate baselines, the opportunity to monitor drug safety, the absence of confounding effect(s) of unreported polydrug abuse and uncontrollable social factors (e.g., expectancy, placebo effects, and peer pressure), which can complicate data interpretation, and cost-effectiveness, animal models, in particular drug self-administration animal models, have been studied extensively in a number of laboratories in several species and have been deemed to be valuable, especially for the evaluation of medications that substitute for or antagonize the effects of cocaine and heroin (Mello et al. (1996), supra).

Example 1

This example demonstrates the synthesis of a decanoate derivative of a hydroxylated analog of vanoxerine.

A decanoate derivative of a hydroxylated analog of vanoxerine, namely compound 5*, scheme 1, page 53, known as (+/−) 1-[2-[bis-(4-fluoro-phenyl)methoxy]ethyl]-4-[3-phenyl-3-hydroxy-propyl] piperazine, otherwise referred to herein as DBL583, was synthesized as shown in Scheme 1.

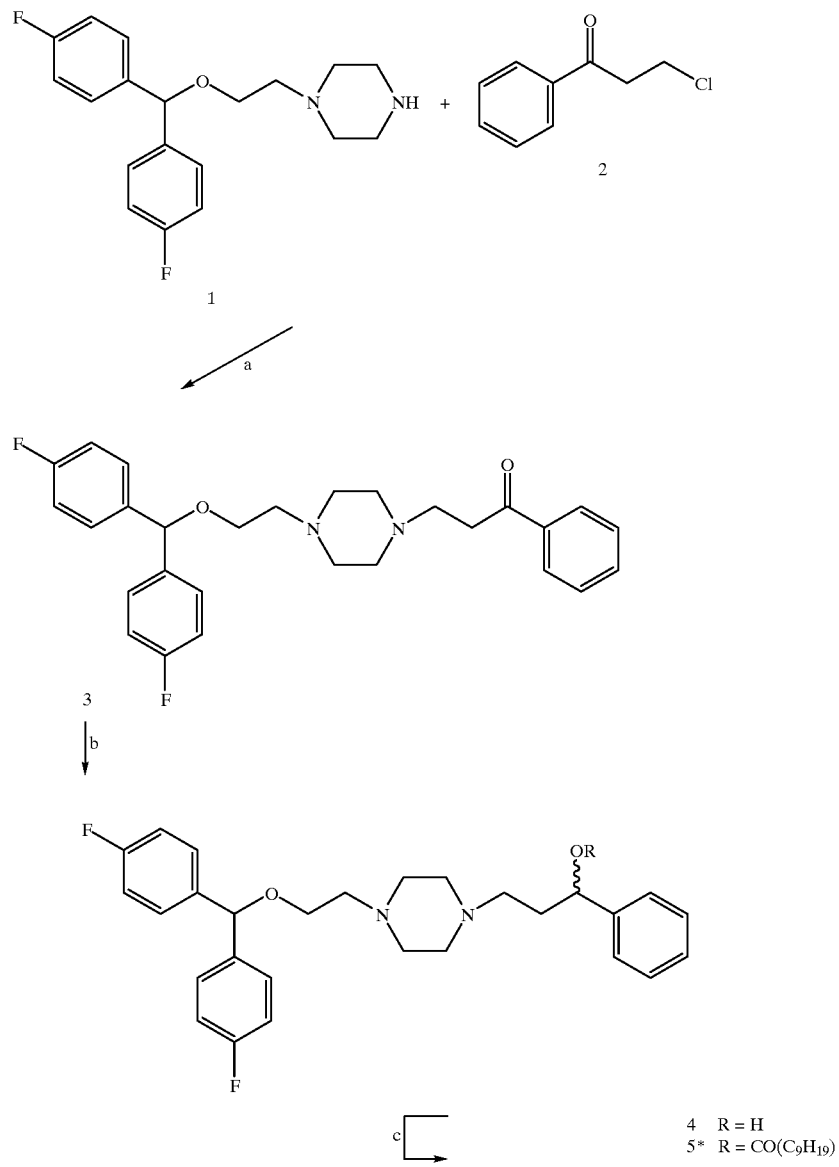

Scheme 1

4  R = H
5*  R = CO($C_9H_{19}$)

Mono-substituted piperazine (1) was condensed with 3-chloropropiophenone (2) to generate a ketone (3; 88% yield after recrystallization as the bis-maleate salt, mp. 165–166° C. (MeOH)). The ketone (3) was easily reduced with lithium aluminum hydride to give a racemate (4; quantitative yield as the bis-HCl salt, mp. 216–218° C. (i-PrOH)). The benzylic alcohol of compound 4 was then treated with a 50% excess of decanoyl chloride in dry ethanol-free chloroform to give the decanoate ester (5*), which was purified by formation of the bis-maleate salt, mp. 154–1550° C. (MeOH), and conversion back to the free base under mild, ammonia-free conditions (5% aq. $NaHCO_3$).

NMR spectra were obtained in $CDCl_3$ using a Varian XL-300 spectrometer. All new compounds gave NMR and mass spectra consistent with their assigned structures and gave C,H,N analysis within ±0.4% of their calculated values. Chemical ionization mass spectra were obtained using a Finnigan 1015 mass spectrometer, and gave the expected molecular ion. Elemental analyses were performed by Atlantic Microlabs (Atlanta, Ga.) and were within ±0.4% of calculated values for the elements indicated. Melting points were determined on a Thomas-Hoover capillary apparatus and were uncorrected.

1-[2[Bis-(p-fluorophenyl)methoxy]ethyl]piperazine (1) was prepared as previously described (van der Zee et al. (1980), supra) and purified as the bis-maleate salt (MeOH); mp 159–160° C.; Lit. 159–161° C. $^1$H NMR ($CDCl_3$): 1.64 (1H, bs, N—H), 2:47 (4H, m, —N—$CH_2$—), 2.65 (2H, t,J=6.0 Hz), 2.88 (4H, t,J=4.9 Hz, NH—$CH_2$—), 5.34 (1H, s, $Ph_2$C—H), 7.00 (4H, t,J=8.7 Hz, ar), 7.25–7.30 (4H, m, ar). Anal ($C_{19}H_{22}N_2OF_2$·2HOOCCHCHCOOH) C,H,N. CIMS 333 (M+1).

1-[2-[Bis-(p-fluorophenyl)methoxy]ethyl]-4-(3-oxo-3 phenylpropyl)piperazine (3) was prepared by adding a solution of 1-[2-[bis-(p-fluorophenyl)methoxy]ethyl]piperazine (26.5 g, 80 mmol; van der Zee et al. (1980), supra) in 200 ml acetone to a stirred solution of 3-chloropropiophenone (23.8 g, 138 mmol) in 150 ml acetone. The reaction was stirred overnight at room temperature and concentrated to an oily residue, which was partitioned between aqueous $NH_4OH$ and chloroform. The organic fraction was washed with water and brine, dried over sodium sulfate and concentrated to a yellow oil. This was dissolved in 800 ml methanol and heated to boiling. Then maleic acid (31.8 g, 274 mmol) was added. The bis-maleate salt was crystallized overnight, collected on a filter, and washed twice with methanol and once with petroleum ether to give 48.6 g of snow-white crystals (70 mmol, 87.5% yield, mp 165–166° C. $^1$H NMR ($CDCl_3$): 2.55 (8H, m, —N—$CH_2CH_2$—N—), 2.67 (2H, t,J=6.0 Hz), 2.84 H, t,J=7.4 Hz), 3.18 (2H, t,J=7.4 Hz), 3.56 (2H, t,J=6.1 Hz), 5.33 (1H, s, $Ph_2$C—H), 7.00 (4H, t,J=8.7 Hz, ar), 7.25–7.29 (4H, m, ar), 7.46 (1H, t,J=7.6 Hz, ar), 7.56 (1H, t,J=7.3 Hz, ar), 7.95 (2H, d,J=7.9 Hz). Anal. ($C_{28}H_{30}N_2O_2F_2$·2HOOCCHCHCOOH) C,H,N. CIMS (M+1).

(±)1-[2-Bis-(p-fluorophenyl)methoxy]ethyl]-4-(3-hyroxy-3-phenylpropyl)piperazine decanoate ester (5*) was prepared by treating a solution of 4 (19.4 g. 42 mmol) in 150 ml dry pentene-stabilized, ethanol-free chloroform with decanoyl chloride (9.65 g. 50 mmol, dissolved in 30 ml chloroform). The reaction was stirred overnight at room temperature under an argon atmosphere. The reaction mixture was concentrated at reduced pressure and the oily product was dissolved in 75 ml of boiling methanol and then treated with maleic acid (11.7 g, 100 mmol). The product was crystallized, collected on a filter, and washed twice with 50 ml portions of petroleum ether to give 29.4 g of snow-white crystals after air-drying (34 mmol, 83% yield), mp 152–154° C. A portion of the bis-maleate salt was converted back to the free base by partition between dilute aqueous $NaHCO_3$ and chloroform. The layers were separated, and the organic fraction was washed with water and brine, dried over sodium sulfate, concentrated, and dried on the vacuum pump at 0.1 mm Hg, to give 17.2 g of compound 5*, free base, as a pale yellow oil. This was dissolved in 300 ml ether, 17.2 g of sesame oil (Sigma Chemical Co., St. Louis, Mo.) were added, and the solution was stirred for 1 hr. The solution was then concentrated at reduced pressure and dried on a vacuum pump (0.1 mm Hg) for 16 hr (until the solution reached constant mass, 34.3 g, calculated as a 49.9% w/w solution in sesame oil) $^1$H NMR ($CDCl_3$): 0.87 (3H t,J=6.7 Hz), 1.24 (12H, bs), 1.60 (2H, t,J=6.9 Hz), 1.87–1.95 (1H, m), 2.03–2.18 (1H, m), 2.31 (2H, t,J=7.5 Hz), 2.43 (4H,m, —N—$CH_2$—), 2.53 (4H,m, —N—$CH_2$—), 2.66 (2H, t,J=6.0 Hz), 3.55 (2H, t,J=6.0 Hz), 5.33 (1H, s, $Ph_2$C—H), 5.81 (1H, t,J=6.9 Hz, C(OCOR)—H), 7.00 (4H, t,J=8.6 Hz, ar), 7.24–7.34 (9H, m, ar) Anal. ($C_{38}H_{50}N_2O_3F_2$·2HOOCCHCHCOOH·1 MeOH) C,H,N. EIMS 621 (M+1).

The results of combustion analysis of the above-described compounds is set forth in Table I.

TABLE I

Combustion Analyses

| Compound | Calculated C | Calculated H | Calculated N | Found C | Found H | Found N |
|---|---|---|---|---|---|---|
| 1 | 57.44 | 5.36 | 4.96 | 57.29 | 5.43 | 4.86 |
| 3 | 62.06 | 5.50 | 4.02 | 61.88 | 5.56 | 4.12 |
| 4 | 62.33 | 6.35 | 5.19 | 62.24 | 6.41 | 5.15 |
| 5* | 63.78 | 7.06 | 3.17 | 63.81 | 6.78 | 3.17 |

Ester 5* was formulated for use in in vivo testing by addition of an equal weight of sesame oil (Sigma) to its ethereal solution, concentration at reduced pressure, and then evacuation at 0.1 Torr until constant mass was reached. The formulated solution was calculated as being a 49.9% w/w solution of compound 5* in sesame oil.

Example 2

This example exemplifies the testing of a present inventive compound for biological activity in vitro.

The biological activity of a given compound in vitro was tested by measuring binding of the compound to the dopamine transporter (DT) and the serotonin transporter (ST) and by measuring the ability of a given compound to inhibit the reuptake of tritiated dopamine ([$^3$H]DA) and tritiated serotonin ([$^3$H]5HT) in accordance with previously described methods (Matecka et al. (1995), supra). Briefly, for binding studies 12×75 mm polystyrene test tubes were prefilled with 100 μl of drug, 100 μl of radioligand ([$^3$H]GBR 12935, i.e., 1-[2-(diphenylmethoxy)ethyl]-4-[3-phenylpropyl] piperazine, or [$^{125}$I]RTI 55 ((−)2β-carbomethoxy-3-β-(4-iodophenyl)nortropane), and 50 ml of a "blocker" or buffer. Drugs and blockers were made up of 55.2 mM sodium phosphate buffer (BB), pH 7.4, containing 1 mg/ml bovine serum albumin (BD/BSA). Radioligands were made up in a protease inhibitor cocktail containing 1 mg/ml BSA (BB containing chymostatin (25 μg/ml), leupeptin (25 μg/ml), EDTA (100 μM) and EGTA (100 μM)). The samples were incubated in triplicate for 18 to 24 hrs at 4° C. (equilibrium) in a final volume of 1 ml. Brandel cell harvesters were used to filter the samples over Whatman GF/B filters, which were presoaked in wash buffer (ice-cold 10 mM Tris-HCl/150 mM NaCl), pH 7.4, containing 2% polyethylenimine.

For [$^3$H]DA and [$^3$H]5HT reuptake assays, synaptosomes were prepared by homogenization of rat caudate (DA) or whole brain minus cerebellum (5HT) in ice-cold 10% sucrose, using a Potter-Elvehjem homogenizer. After 1000×g centrifugation for 10 min at 4° C., the supernatants were retained on ice. The reuptake assays were initiated by the addition of 100 μl of synaptosomes to 12×75 mm polystyrene test tubes, which were prefilled with 750 μl of [$^3$H]ligand (5 nM final concentration) in a Krebs-phosphate phosphate buffer (pH 7.4), which contained ascorbic acid (1 mg/ml) and pargyline (50 μM) (buffer), 100 μl of test drugs made up in buffer, and 50 μl of buffer. The nonspecific reuptake of each [$^3$H]ligand was measured by incubation in the presence of 1 μM GBR 12909 ([$^3$H]DA) and 10 μM fluoxetine ([$^3$H]5HT). The incubations were terminated after a 20 min ([$^3$H]DA) or 30 min ([$^3$H]5HT) incubation at 25° C. by adding 4 ml of wash buffer (10 mM Tris-HCl, pH 7.4, containing 0.9% NaCl at 25° C.), followed by rapid filtration over Whatman GF/B filters and one additional wash cycle. The Krebs-phosphate buffer contained 154.5 mM NaCl, 2.9 mM KCl, 1.1 mM $CaCl_2$, 0.83 mM $MgCl_2$ and 5 mM glucose. The tritium retained on the filters was counted in a Taurus beta counter after an overnight extraction into ICN Cytoscint cocktail.

Initial experiments were conducted to determine the appropriate concentration range of each test agent at each binding site. After this, eight-point inhibition curves, ranging from 90% to 10% of control, were generated. The data of two separate experiments were pooled, and fit, using a two-parameter logistic equation to determine the best-fit estimates of the $IC_{50}$ and slope. The $K_m$ values for [$^3$H]5HT and [$^3$H]DA reuptake were 17.4±0.8 nM and 38.3±1.6 nM, respectively. The $K_d$ values for [$^3$H]GBR 12935 and [$^{125}$I] RTI 55 binding were 1.35±0.14 nM and 0.91±0.04 nM, respectively. Binding data for the parent compound 4 are shown in Table II, along with the corresponding data for GER 12909.

TABLE II

| Compound | [$^3$H] DA reuptake (nM) | [$^3$H] 5HT reuptake (nM) | DAT labeled [$^{125}$I] RTI 55 binding (nM) | SERT labeled [$^{125}$I] RTI 55 binding (nM) |
|---|---|---|---|---|
| GBR 12909 | 4.3 | 73 | 3.7 | 127 |
| 4 | 5.6 | 69 | 2 | 117 |

Example 3

This example exemplifies the testing of a present inventive compound in vivo with respect to cocaine.

Seven adult, male rhesus monkeys, weighing between 7.5–9.0 kg, served as subjects. Each had been previously trained under fixed ratio (FR) schedules of food and cocaine self-administration, had prior experience with a variety of dopaminergic drugs, and was maintained at 90% of its ad libitum weight by supplemental food. Experiments were conducted in sound- and light-attenuating chamber (Glowa et al. (1995a and b), supra).

Food (1 g banana pellets) was delivered by a dispenser in front of the monkey. Cocaine was delivered through the momentary activation of a syringe driver, which connected a drug supply to a subcutaneous vascular access port (Wojnicki et al., Lab. Anim. Med. 44: 491–494 (1994)). Schedules were programmed on a MED-PC system and performances were monitored using cumulative recorders.

Responding was maintained under a multiple FR of 30-response food (FR30 food), 30-response cocaine (FR30 cocaine), and 10-min time-out (TO) schedule (Glowa et al. (1995a and b), supra). In the presence of blue stimulus lights, 30 responses produced food. In the presence of red stimulus lights, 30 responses produced a cocaine infusion (10 μg/kg). Availability of food or cocaine alternated during brief periods of a 2-hr session. In each period, a maximum of 10 reinforcer deliveries could be produced. Availability of each reinforcer was constrained by a 60-sec limited hold. Periods of food and drug availability were separated by a 10-min TO and sessions always began with a food component. Once responding was stable (±20% over at least eight to ten days of consecutive sessions), the monkeys were injected intramuscularly (thigh muscle) with 0, 1, 3 or 6 ml of 50% w/w solution of compound 5* in sesame oil. Thus, a 6 cc injection consisted of 3 g of compound 5* and 3 g of sesame oil. Immediately after injection, the monkey was run in a daily experimental session. Two monkeys were studied per dose, except for the 1 ml dose. Behavioral data were collected as the session average rate of responding for each component (food or cocaine) during individual daily sessions. Control rates were determined by averaging individual rates over the period immediately before treatment. Drug effects are described as the mean of individual effects (percent of control rates for both food- and cocaine-maintained responding) as a function of the dose of compound 5*. Data for the first 24 days of treatment were statistically analyzed by repeated-measure ANOVA, and subsequently partitioned by two-factor repeated-measure ANOVA.

Prior to treatment, absolute control rates of responding (mean; coeff. var.) were comparable for food-(3.696 resp/sec; ±9.99%) and cocaine-(4.026 resp/sec; ±13.6%) maintained responding. Three-factor ANOVA determined a significant main effect of dose (F=11.031; p=0.016), event (F=13.558; p=0.0059) and days of treatment (F=7.905; p=0.0208).

FIG. 1, which is a graph of effect (% of control) versus dose of decanoate (DBL583, ml intramuscularly), shows the mean effect of treatment at each dose over the first 24 days immediately following a single injection. Non-injection control values were stable over this treatment period with food- and cocaine-maintained responding averaging 99.9% and 100.4% of control, respectively. The lowest dose of compound 5* had no effect on food-maintained responding (97% of control) and slightly decreased (76.2% of control) cocaine-maintained responding, although a downward trend in drug-maintained responding was clearer during the second and third week following the injection and recovered to baseline levels on subsequent days. An intermediate dose (3 ml) of compound 5* had a slight overall effect (82% control) on food-maintained responding and decreased cocaine-maintained responding to about 74% of control over the entire treatment period. There were no differences in effect on food- and cocaine-maintained responding at these lower doses. In contrast, the highest dose of compound 5* tested (6 ml) had no effect on food-maintained responding and decreased cocaine-maintained responding to 25.3% of control over the entire treatment period.

Figure 2:
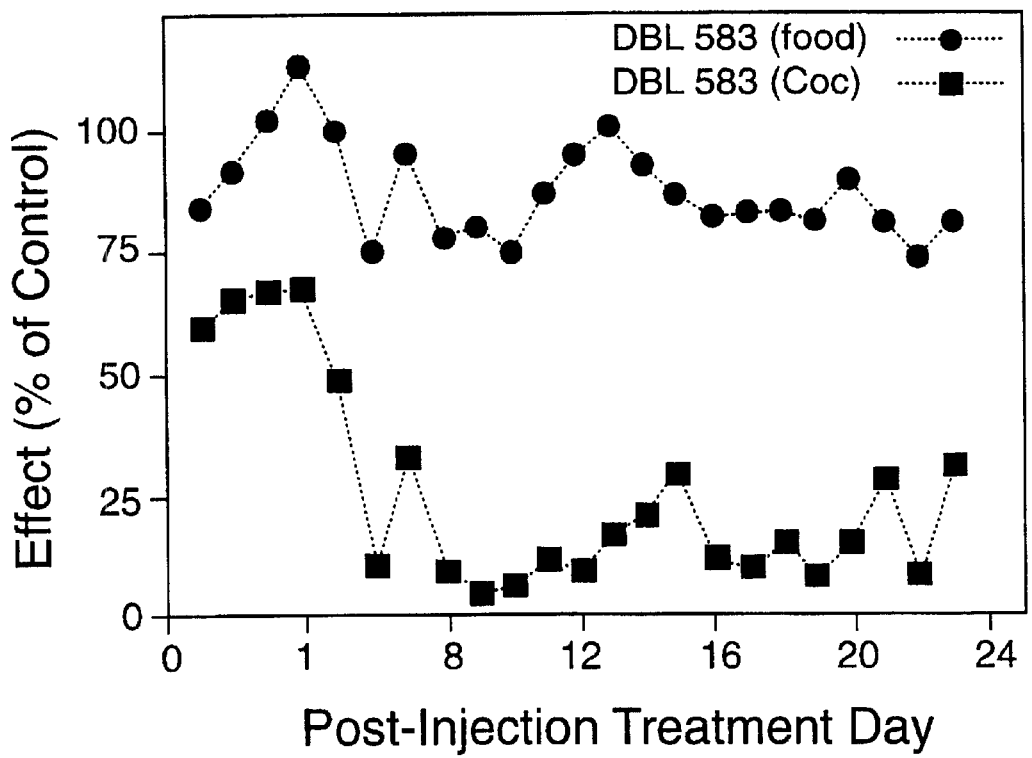
FIG. 2 is a graph of effect (% of control) versus post-injection treatment day, which illustrates the mean effects of a 6 ml dose of compound 5* on responding maintained by food and cocaine in rhesus monkeys over 24 days of treatment. The effects are expressed as the mean percent of control rates for food-maintained responding and cocaine-maintained responding, wherein n=2.

FIG. 2, which is a graph of effect (% of control) versus post-injection treatment day, shows that the effect of compound 5* on cocaine-maintained responding was observable during the first five days after the injection. However, exclusion of these days resulted in a robust statistical difference (F=55.919; p=0.017) in the effect of compound 5* on food- and cocaine-maintained responding over the remaining treatment period. Following the treatment period, cocaine-maintained responding recovered to control levels.

Administration of the compound DL205, which is the compound according to general structural Formula 3, wherein $R_3$ is 4-OH, a, b and c are all single bonds, and $R_1$ and $R_2$ are each 4-fluoro, under the same conditions eliminated 42% of food-maintained responding (as a percent of control) and 41% of cocaine-maintained responding (as a percent of control) at a dose of 1.7 mg/kg. When the dose was increased to 3.0 mg/kg, 31% of food-maintained responding and 14% of cocaine-maintained responding was eliminated.

The current results show that a single treatment with a relatively selective DA reuptake inhibitor, formulated to be long-acting, resulted in a sustained and selective effect on cocaine-maintained responding for almost thirty days as compared to about 4–6 hrs for vanoxerine. These results are qualitatively and quantitatively similar to those obtained with both acute and repeated daily administration of shorter-acting DA reuptake inhibitors, except only a single injection was required (Glowa et al. (1995a and b), supra). Thus, drug-seeking behavior can be suppressed for periods assumed to be concordant with the pharmacological half-life of the decanoate preparation. These results are of particular interest because they appear to be consistent with those expected of a long-term medication for drug abuse, in that drug-seeking was selectively decreased for a relatively long time. An interesting observation of the current effects is that the decanoate required several days to obtain full effect. This observation is of interest because it suggests the slow onset of similar agents may limit their abuse potential. Previous studies have shown that by decreasing the onset of self-administered cocaine, animals responding for a drug will decline. This decrement in the reinforcing effects of cocaine, presumably mediated by delayed reinforcement, is likely to be a desired effect of formulating a slow-onsetting, long-acting, antagonist-based medication.

Example 4

This example exemplifies the testing of a present inventive compound in vivo with respect to methamphetamine.

The in vivo microdialysis experiments were performed according to published procedures (Baumann et al., *J. Pharmacol. Exp. Ther.*, 271:1216–1222 (1994)). Briefly, male Sprague-Dawley rats (Charles River, Wilmington, Mass.) were anesthetized with Equithesin (3 ml/kg). Rats were fitted with indwelling jugular catheters and intracerebral guide cannulae (CMA 12, Bioanalytical Systems, Inc., West Lafayette, Ill.) aimed at the nucleus accumbens (ML±1.5, AP +1.6, DV +6.2 relative to bregma) (Paxinos, G., *The Rat Brain in Stereotaxic Coordinates*, New York: Academic Press, 1982.). After 7–10 days, rats were lightly anesthetized with metofane. Microdialysis probes (CMA/12, 2 mm×0.5 mm, BAS) were lowered into guide cannulae and polyethylene extensions were attached to jugular catheters. Artificial Ringers' solution (147.0 mM NaCl, 4.0 mM KCl, 2.0 mM $CaCl_2$, unadjusted pH 6.5) was pumped through the probe at 0.5 µl/min. Beginning 2–3 hr after probe insertion, 10 µl dialysate samples were collected at 20 min intervals and immediately assayed for dopamine (DA) and serotonin (5-HT) by microbore HPLC-EC (high pressure-liquid chromatography with electrochemical detection) (Baumann et al. (1994), supra). The first 3 samples collected before any treatment were considered baseline samples, and all subsequent monoamine measures were expressed as a percent of this baseline.

Figure 3:
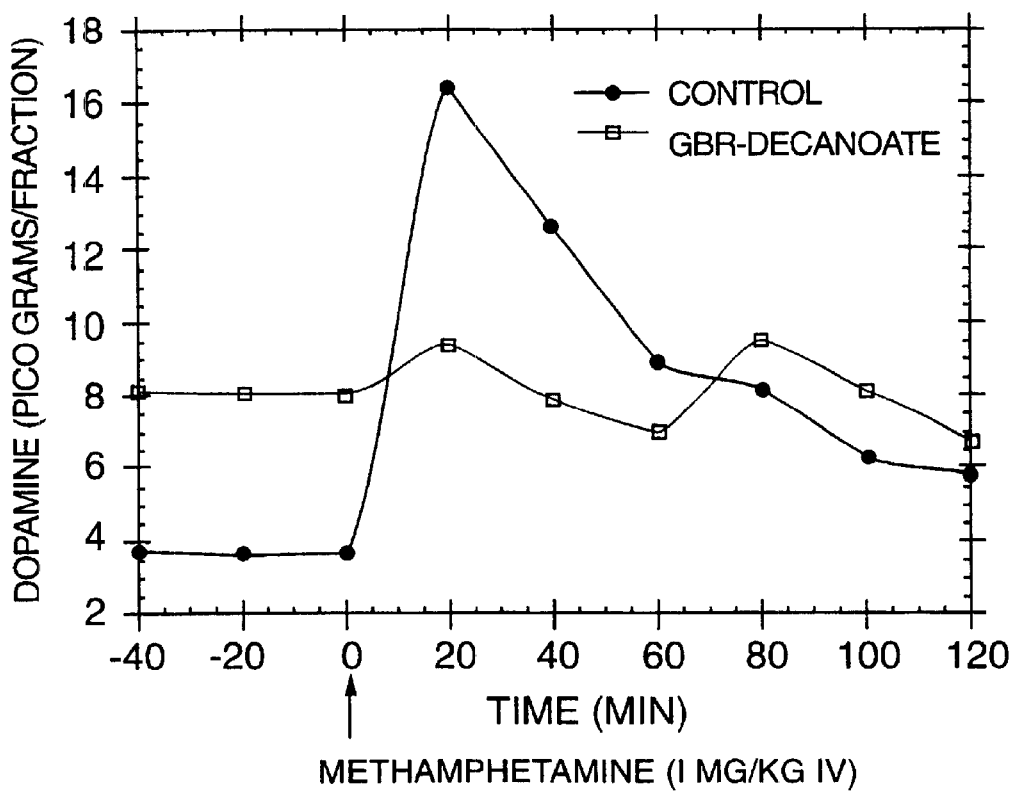
FIG. 3 is a graph of dopamine (picogram/fraction) versus methamphetamine (1 mg/kg IV) over time (min), which illustrates that compound 5* increased basal levels of dopamine two-fold and essentially eliminated the ability of methamphetamine to increase dopamine levels.
Figure 4:
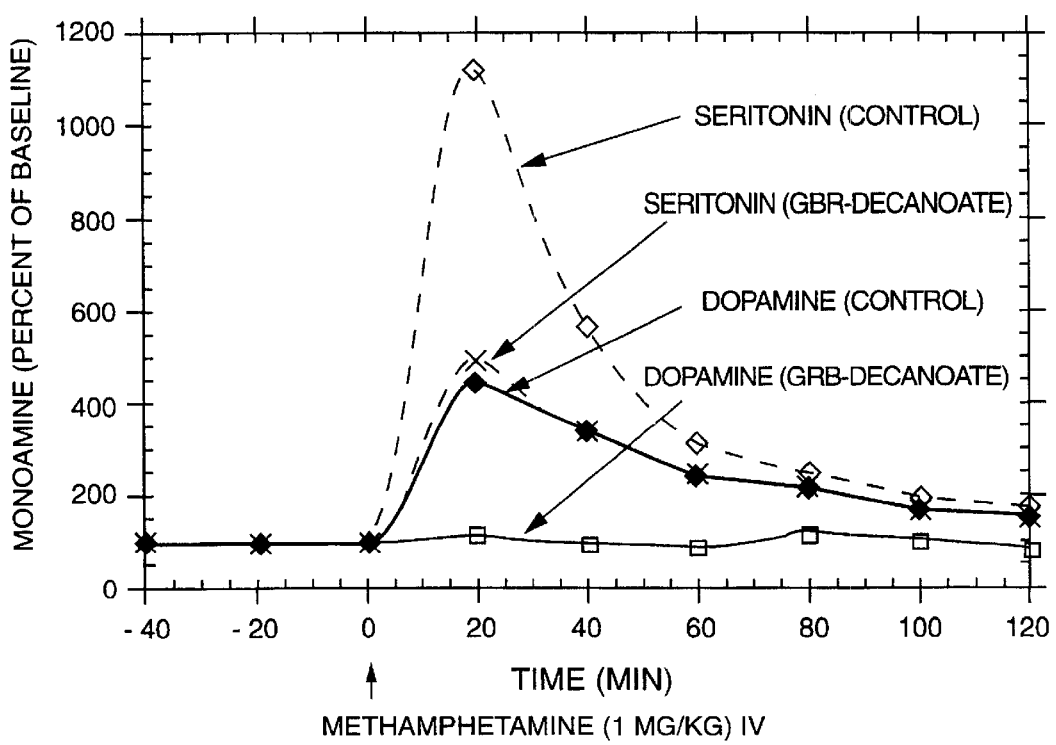
FIG. 4 is a graph of monoamine (percent of baseline) versus methamphetamine (1 mg/kg IV) over time (min), which illustrates that compound 5* blunted the ability of methamphetamine to increase dopamine (DA) and serotonin (5-HT).

On the first day of the experiment, rats (n=4) received an injection of methamphetamine (1 mg/kg iv). After samples were collected for 120 minutes, rats were injected with Compound 5* (0.7 ml/kg im). Four days later, rats received a second injection of methamphetamine. The results are summarized in FIGS. 3 and 4. FIG. 3 is a graph of dopamine picogram/fraction) versus methamphetamine (1 mg/kg IV) over time (min), which illustrates that compound 5* increased basal levels of dopamine (DA) two-fold and essentially eliminated the ability of methamphetamine to increase dopamine levels. FIG. 4 is a graph of monoamine (percent of baseline) versus methamphetamine (1 mg/kg IV) over time (min), which illustrates that compound 5* blunted the ability of methamphetamine to increase dopamine and serotonin (5-HT). These results demonstrate that the present inventive compounds can be used to treat methamphetamine or amphetamine abuse.

All publications cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A compound selected from the group consisting of:
   1-[2-[bis-(4-fluorophenyl)methoxy]ethyl]-4-[3-phenyl-3-hydroxypropyl]piperazine,
   1-[2-[bis-(4-fluorophenyl)methoxy]ethyl]-4-[3-phenyl-2-hydroxypropyl]piperazine,
   1-[2-[bis-(4-fluorophenyl)methoxy]ethyl]-4-[3-(2-hydroxy-phenyl)-propyl]piperazine,
   1-[2-[bis-(4-fluorophenyl)methoxy]ethyl]-4-[3-(3-hydroxy-phenyl)-propyl]piperazine, and
   1-[2-[bis-(4-fluorophenyl)methoxy]ethyl]-4-[3-(4-hydroxy-phenyl)-propyl]piperazine,
   in which said hydroxy substituent is esterified with an alkanoic acid comprising a $C_{6-20}$ alkyl, a $C_{6-20}$ aryl alkyl or a $C_{6-20}$ cycloalkyl alkyl.

2. The compound of claim 1, wherein said compound is 1-[2-[bis-(4-fluorophenyl)methoxy]ethyl]-4-[3-phenyl-3-hydroxypropyl]piperazine in which said hydroxy substituent is esterified with a decanoic acid.

3. A compound of formula 1:

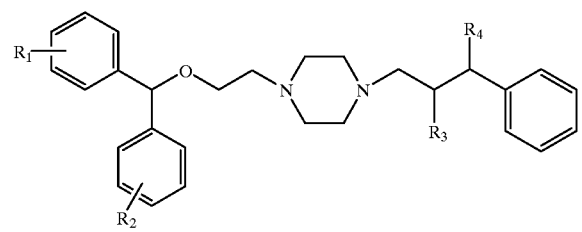

FORMULA 1 wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, wherein at least one of $R_3$ and $R_4$ is hydroxyl and the other is hydrogen or hydroxyl, wherein at least one hydroxyl at $R_3$ or $R_4$ is esterified with an alkanoic acid comprising a $C_{6-20}$ alkyl, a $C_{6-20}$ aryl alkyl or a $C_{6-20}$ cycloalkyl alkyl, and the stereochemistry of $R_3$ and $R_4$ is R, S or RS.

4. A compound of formula 14:

FORMULA 14

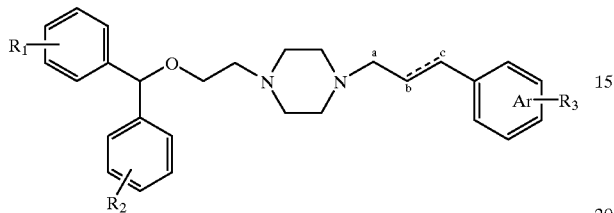

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, $R_3$ is 2-, 3-, or 4-hydroxyl, Ar can comprise from 1 to 4 atoms selected from the group consisting of O, N and S, b—c is a single, double (cis or trans) or triple bond, and wherein at least one hydroxyl is esterified with an alkanoic acid comprising a $C_{6-20}$ alkyl, a $C_{6-20}$ aryl alkyl or a $C_{6-20}$ cycloalkyl alkyl.

5. The compound of claim 4, wherein said Ar is selected from the group consisting of pyridine and pyrazine.

6. A compound of formula 5:

FORMULA 5

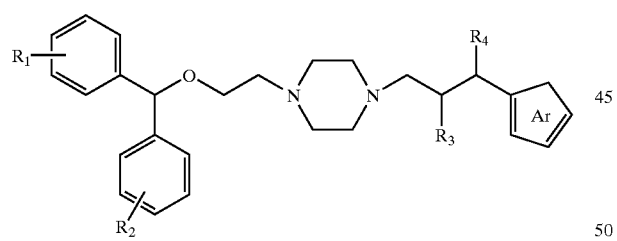

or formula 6:

FORMULA 6

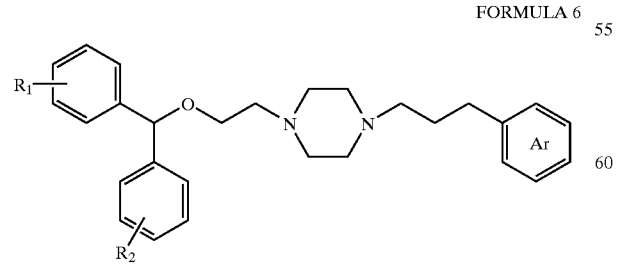

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, wherein at least one of $R_3$ and $R_4$ is a hydroxyl and the other is hydrogen or hydroxyl, Ar contains from 1 to 4 atoms selected from the group consisting of O, N and S, wherein at least one hydroxyl at $R_3$ or $R_4$ is esterified with an alkanoic acid comprising a $C_{6-20}$ alkyl, a $C_{6-20}$ aryl alkyl or a $C_{6-20}$ cycloalkyl alkyl, and the stereochemistry of $R_3$ and $R_4$ is R, S or RS.

7. The compound of claim 6, wherein Ar of formula 5 is selected from the group consisting of thiophene, furan, imidazole and tetrazole, and Ar of formula 6 is selected from the group consisting of pyridine and pyrazine.

8. A compound of formula 7:

FORMULA 7

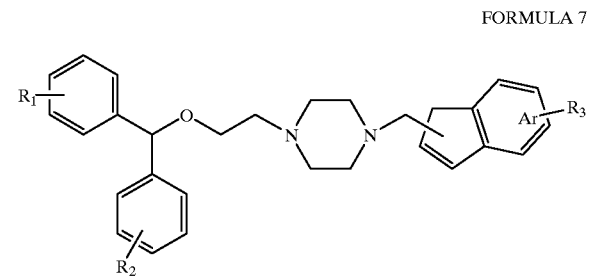

or formula 8:

FORMULA 8

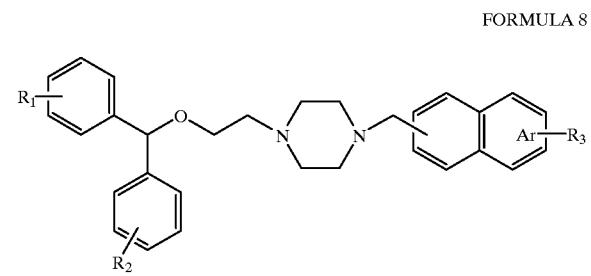

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, Ar contains from 1 to 4 atoms selected from the group consisting of O, N and S, $R_3$ is hydroxyl at any one or more of positions 1–7 of Ar of formula 7 and at any one or more of positions 1–8 of Ar of formula 8, and wherein at least one hydroxyl is esterified with an alkanoic acid comprising a $C_{6-20}$ alkyl, a $C_{6-20}$ aryl alkyl or a $C_{6-20}$ cycloalkyl alkyl.

9. The compound of claim 8, wherein Ar of formula 7 is selected from the group consisting of indole, benzofuran and benzoxazole and Ar of formula 8 is selected from the group consisting of quinoline and isoquinoline.

10. A compound of formula 9:

FORMULA 9

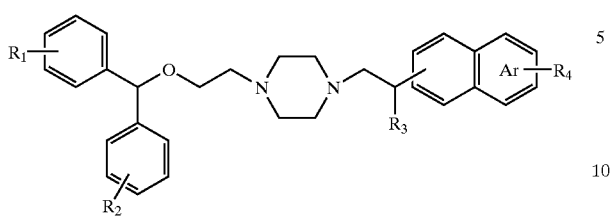

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, $R_3$ is hydrogen or hydroxyl, the stereochemistry of which is R, S or RS, Ar contains from 1 to 4 atoms selected from the group consisting of O, N and S, $R_4$ is hydroxyl at any one or more of positions 1–8 of Ar, and wherein at least one hydroxyl is esterified with an alkanoic acid comprising a $C_{6-20}$ alkyl, a $C_{6-20}$ aryl alkyl or a $C_{6-20}$ cycloalkyl alkyl.

11. A compound of formula 10:

FORMULA 10

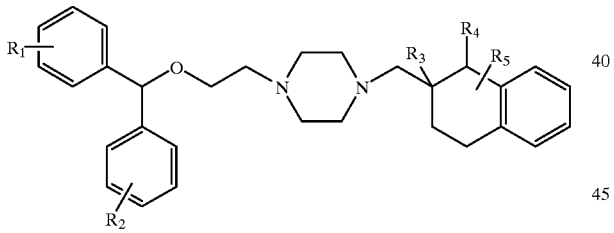

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, $R_3$ is hydrogen or $C_{1-7}$ alkyl, $R_4$ is hydroxyl, $R_5$ is hydrogen, $C_{1-7}$ alkyl, aryl or aryl alkyl, wherein the stereochemistry of $R_3$, $R_4$ and $R_5$ is R, S, or RS, and wherein at least one hydroxyl is esterified with an alkanoic acid comprising a $C_{6-20}$ alkyl, a $C_{6-20}$ aryl alkyl or a $C_{6-20}$ cycloalkyl alkyl.

12. A compound of formula 11:

FORMULA 11

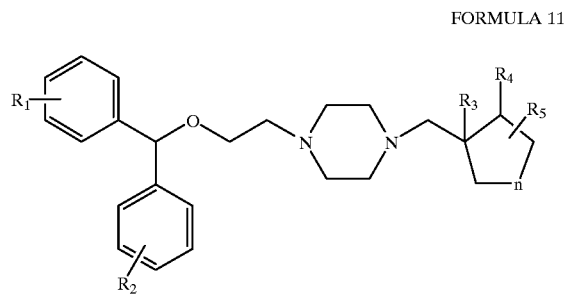

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, $R_3$ is hydrogen, $R_4$ is hydroxyl, $R_5$ is hydrogen, $C_{1-7}$ alkyl, aryl or aryl alkyl, n is $(CH_2)$, $(CH_2)_2$ or $(CH_2)_3$ and can be substituted with $R_5$, wherein the stereochemistry of $R_3$, $R_4$ and $R_5$ is R, S, or RS, and wherein at least one hydroxyl is esterified with an alkanoic acid comprising a $C_{6-20}$ alkyl, a $C_{6-20}$ aryl alkyl or a $C_{6-20}$ cycloalkyl alkyl.

13. A compound of formula 12:

FORMULA 12

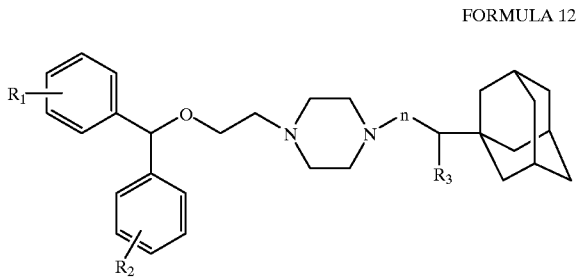

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, $R_3$ is hydroxyl, n is $(CH_2)$, $(CH_2)_2$ or $(CH_2)_3$, wherein the stereochemistry of $R_3$ is R, S or RS, and wherein at least one hydroxyl is esterified with an alkanoic acid comprising a $C_{6-20}$ alkyl, a $C_{6-20}$ aryl alkyl or a $C_{6-20}$ cycloalkyl alkyl.

14. A compound of formula 13:

FORMULA 13

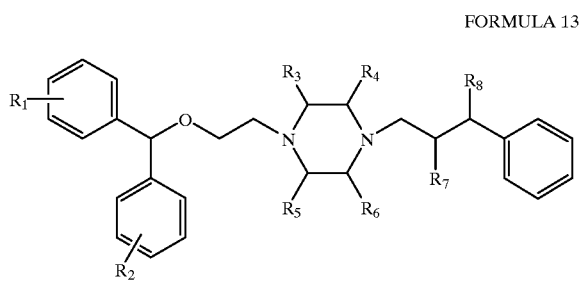

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, each of $R_3$–$R_6$ is hydrogen, hydroxyl, $C_{1-7}$ alkyl, cycloalkyl, cycloalkyl alkyl, halo, halo $C_{1-7}$ alkyl, $C_{1-7}$ alkoxy, hydroxy $C_{1-7}$ alkyl, $C_{2-7}$ alkenyl, and $C_{2-7}$ lower alkynyl, each of $R_7$ and $R_8$ is hydrogen or hydroxyl, wherein the stereochemistry of $R_3$–$R_8$ is R, S, or RS, and wherein at least one of $R_1$, $R_2$, $R_7$ and $R_8$ is hydroxyl and at least one hydroxyl is esterified with an alkanoic acid comprising a $C_{6-20}$ alkyl, a $C_{6-20}$ aryl alkyl or a $C_{6-20}$ cycloalkyl alkyl.

15. A compound of formula 15:

FORMULA 15

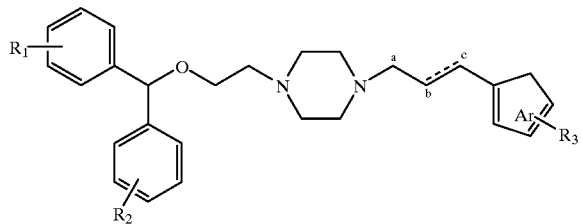

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, $R_3$ is hydroxyl at any one or more of positions 2–5, Ar can contain 1–3 atoms selected from the group consisting of O, N and S, b—c is a single, double (cis or trans) or triple bond, and wherein at least one hydroxyl is esterified with an alkanoic acid comprising a $C_{6-20}$ alkyl, a $C_{6-20}$ aryl alkyl or a $C_{6-20}$ cycloalkyl alkyl.

16. The compound of claim 15, wherein Ar is selected from the group consisting of thiophene, furan and imidazole.

17. A compound of the formula:

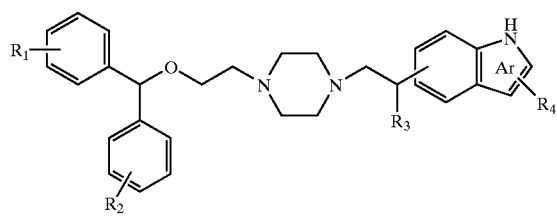

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, $R_3$ is hydrogen or hydroxyl, the stereochemistry of which is R, S or RS, $R_4$ is hydroxyl at any one or more of positions 1–7 of Ar, and wherein at least one hydroxyl is esterified with an alkanoic acid comprising a $C_{6-20}$ alkyl, a $C_{6-20}$ aryl alkyl or a $C_{6-20}$ cycloalkyl alkyl.

18. A compound of the formula:

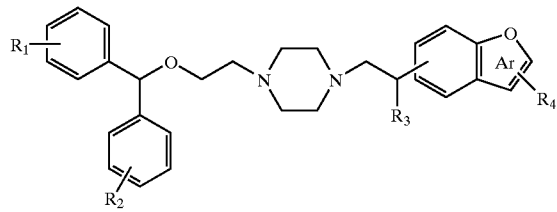

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, $R_3$ is hydrogen or hydroxyl, the stereochemistry of which is R, S or RS, $R_4$ is hydroxyl at any one or more of positions 1–7 of Ar, and wherein at least one hydroxyl is esterified with an alkanoic acid comprising a $C_{6-20}$ alkyl, a $C_{6-20}$ aryl alkyl or a $C_{6-20}$ cycloalkyl alkyl.

19. A compound of the formula:

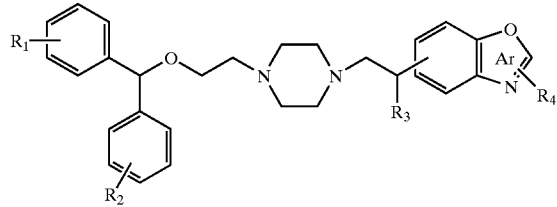

wherein each of $R_1$ and $R_2$ is one or more of the substituents selected from the group consisting of hydrogen, hydroxyl, a $C_{1-7}$ alkyl, a cycloalkyl, a cycloalkyl alkyl, a $C_{1-7}$ alkoxy, halo, a halo $C_{1-7}$ alkyl, a hydroxy $C_{1-7}$ alkyl, an amino, a $C_{1-7}$ alkyl mono amino, a $C_{1-7}$ alkyl di amino, a $C_{1-7}$ alkanoyl, a $C_{2-7}$ alkenyl, and a $C_{2-7}$ alkynyl, R₃ is hydrogen or hydroxyl, the stereochemistry of which is R, S or RS, R₄ is hydroxyl at any one or more of positions 1–7 of Ar, and wherein at least one hydroxyl is esterified with an alkanoic acid comprising a $C_{6-20}$ alkyl, a $C_{6-20}$ aryl alkyl or a $C_{6-20}$ cycloalkyl alkyl.

20. A pharmaceutical composition comprising a compound of claim 1 and a pharmaceutically acceptable carrier.

21. The pharmaceutical composition of claim 20, wherein said composition is suitable for depot injection at a site selected from the group consisting of buttocks and thigh.

22. The pharmaceutical composition of claim 20, wherein said compound is released from said composition over a period of at least about 30 days.

23. A pharmaceutical composition comprising a compound of claim 2 and a pharmaceutically acceptable carrier.

24. A method of binding a compound to the dopamine transporter in an individual who abuses cocaine, which method comprises administering to said individual the compound of claim 1 in an amount sufficient to antagonize the effects of cocaine.

25. The method of claim 24, wherein said compound is administered by depot injection into a site selected from the group consisting of buttocks and thigh.

26. A method of binding a compound to the dopamine transporter in an individual who abuses cocaine, which method comprises administering to said individual the compound of claim 2 in an amount sufficient to antagonize the effects of cocaine.

27. A method of administering the compound of claim 1 to an individual who abuses cocaine, which method comprises administering to said individual a compound of claim 1 in an amount sufficient to antagonize the effects of cocaine in said individual during the sustained release of said compound in said individual.

28. The method of claim 27, wherein said compound is administered by depot injection into a site selected from the group consisting of buttocks and thigh.

29. The method of claim 27, wherein said sustained release is for a period of time of at least about 30 days.

30. A method of administering the compound of claim 2 to an individual who abuses cocaine, which method comprises administering to said individual a compound of claim 2 in an amount sufficient to antagonize the effects of cocaine in said individual during the sustained release of said compound in said individual.

31. A method of administering the compound of claim 1 to an individual who abuses methamphetamine or amphetamine, which method comprises injecting to said individual by depot injection at a site selected from the group consisting of buttocks and thigh a pharmaceutical composition that can be depot injected, said composition comprising the compound of claim 1, in an amount sufficient to antagonize said methamphetamine or amphetamine in said individual during the sustained release of said compound in such individual for a period of time of at least about 30 days.

32. A method of administering the compound of claim 2 to an individual who abuses methamphetamine or amphetamine, which method comprises injecting to said individual by depot injection at a site selected from the group consisting of buttocks and thigh a pharmaceutical composition that can be depot injected, said composition comprising the compound of claim 2, in an amount sufficient to antagonize said methamphetamine or amphetamine in said individual during the sustained release of said compound in such individual for a period of time of at least about 30 days.

33. The method of claim 30, wherein said compound is administered by depot injection into a site selected from the group consisting of buttocks and thigh.

34. The method of claim 30, wherein said sustained release is for a period of time of at least about 30 days.

* * * * *